United States Patent [19]

Chen et al.

[11] Patent Number: 4,677,069

[45] Date of Patent: Jun. 30, 1987

[54] CLAM DERIVED PROTEINASES

[75] Inventors: Hung-Chang Chen, Elmsford; Robert R. Zall, Ithaca, both of N.Y.

[73] Assignee: Cornell Research Foundation, Inc., Ithaca, N.Y.

[21] Appl. No.: 683,108

[22] Filed: Dec. 18, 1984

[51] Int. Cl.[4] .......................... C12N 9/64; C12N 9/50; A23C 19/04; A23L 1/31

[52] U.S. Cl. ..................................... 435/226; 426/36; 426/56; 426/63; 435/219; 435/815; 435/816

[58] Field of Search ............... 435/212, 219, 226, 815, 435/816; 426/36, 56, 63

[56] References Cited

PUBLICATIONS

Characterization and Select Applications of Proteolytic Enzymes Extracted and Purified with Clam Viscera; Ph. D. Thesis of Hung-Chang Chen, dated Aug. 1984.
Reid and Rauchert, 1970, Comp. Biochem. and Physiol., 35:689–695.
Reid and Rauchert, 1972, Comp. Biochem. and Physiol., 41A:887–895.
Cockburn and Reid, 1980, Comp. Biochem. and Physiol., 65B:275–281.
Reid and Rauchert, 1976, Comp. Biochem. and Physiol., 54B:467–472.
Dumitru et al, 1977, Revue Roumaine Biochem., 14:95–100.
Dumitru et al, 1978, Comp. Biochem. and Physiol., 59B:81–85.
Jordachescu et al, 1978, Comp. Biochem. and Physiol., 61B:119–122.
Dumitru et al, 1975, Revue Roumaine Biochem., 12:159–165.
Reid, 1978, Veliger, 20:260–265.
Sakai et al, 1979, Comp. Biochem. Physiol., 62B:269–273.
Reid, 1977, Comp. Biochem. Physiol., 59A:573–575.
Noda et al, 1982, Agric. Biol. Chem., 46:1565–1569.
Barrett and Kirschke, 1981, Methods in Enzymology, 80:535–581.
Barrett, 1977, Proteinases in Mammalian Cells and Tissues, Chapter 4, Elsevier/N. Holland Biomed. Press.
Barrett, 1973, Biochem. J., 131:809–822.
Barrett, 1977, Proteinases in Mammalian Cells and Tissues, Chapter 5, Elsevier/N. Holland Biomed. Press.
Dingle et al, 1971, Biochem. J., 123:1–13.
Yago et al, 1975, J. Biolog. Chem., 250:4749–4754.
Sapolsky et al, 1972, J. Biolog. Chem., 247:2069–2076.
Penny et al, 1974, J. Sci. Fd. Agric., 25:703–708.
Penny et al, 1980, Dev. Meat Sci., 1:115–143.
Schwartz et al, 1977, Biochem. J., 167:811–820.
Etherington et al, 1977, Acta Biol. Med. Germ., 36:1555–1563.
Bird et al, 1977, Acta Biol. Med. Germ., 36:1587–1604.
Chen et al, J. Food Science, 51(1):71–75 and 78, 1986.
Chen et al, J. Food Science, 51(3):815–820 and 825, 1986.

*Primary Examiner*—David M. Naff
*Attorney, Agent, or Firm*—Jones, Tullar & Cooper

[57] ABSTRACT

This invention relates to three enzymes, their isolation from the viscera of bivalves, e.g. the surf clam or cherrystone clam, their characterization and uses. The first two are carboxyl proteinases having molecular weights of about 77,200 and about 36,700 and display activity similar to mammalian D-cathepins. The third is a thiol proteinase having a molecular weight of about 17,400 and displays activity similar to mammalian B-cathepins. In addition to attaching various substrates, the enzymes coagulate cheese milk and tenderize meat.

5 Claims, 9 Drawing Figures

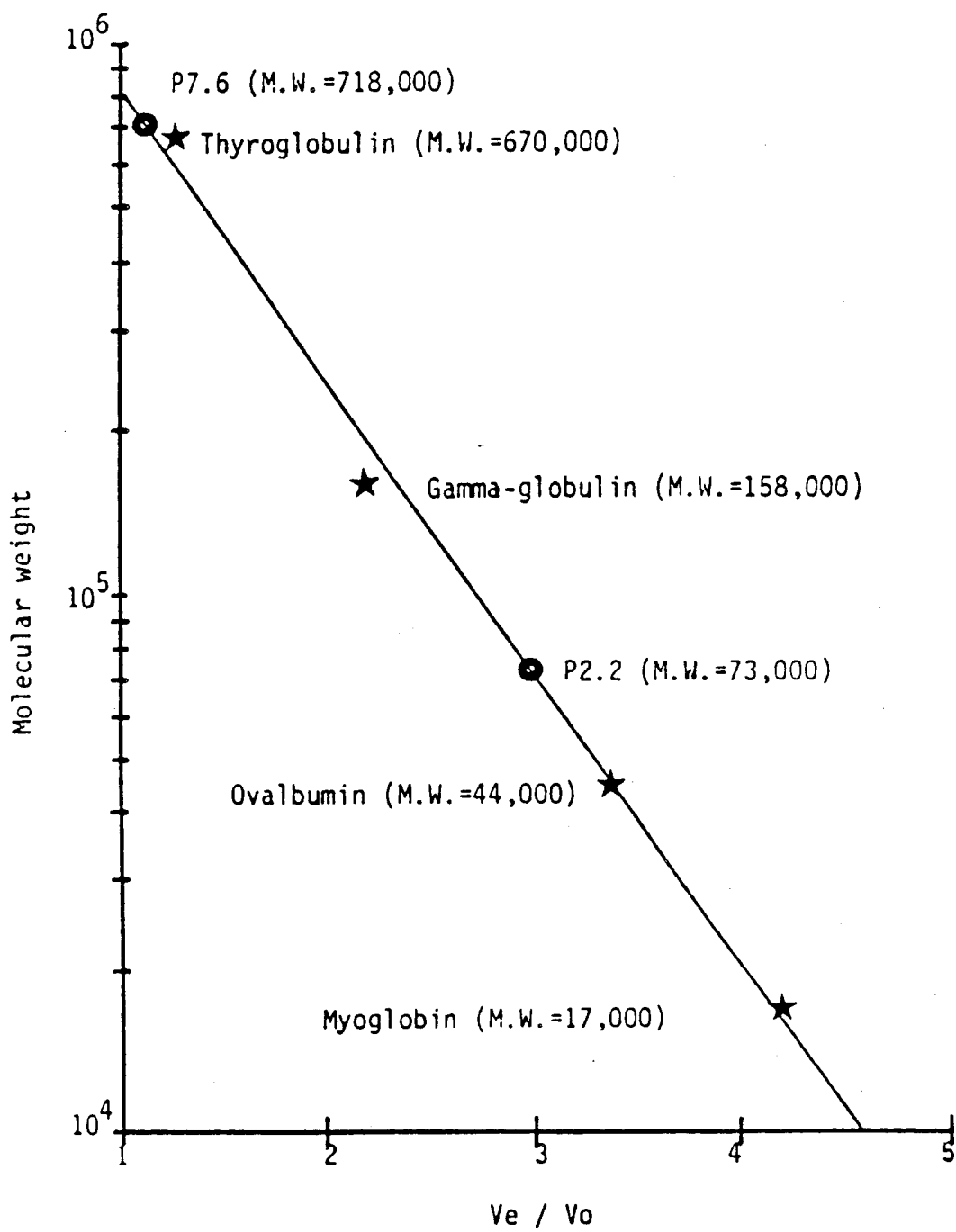
FIG. 1 Molecular weight estimation of proteolytic enzymes in the crude extract from fresh viscera of cherrystone clam

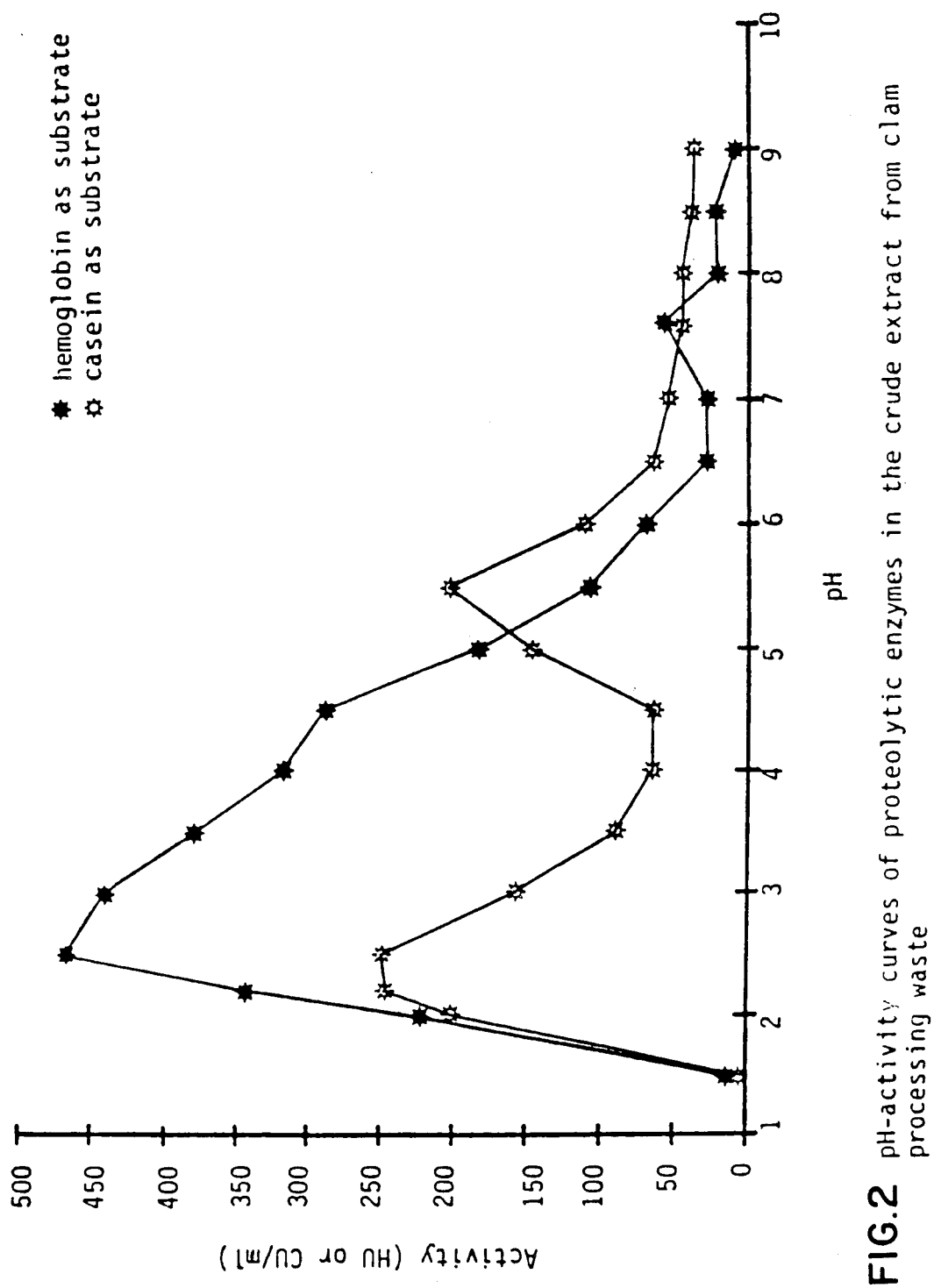
FIG. 2 pH-activity curves of proteolytic enzymes in the crude extract from clam processing waste

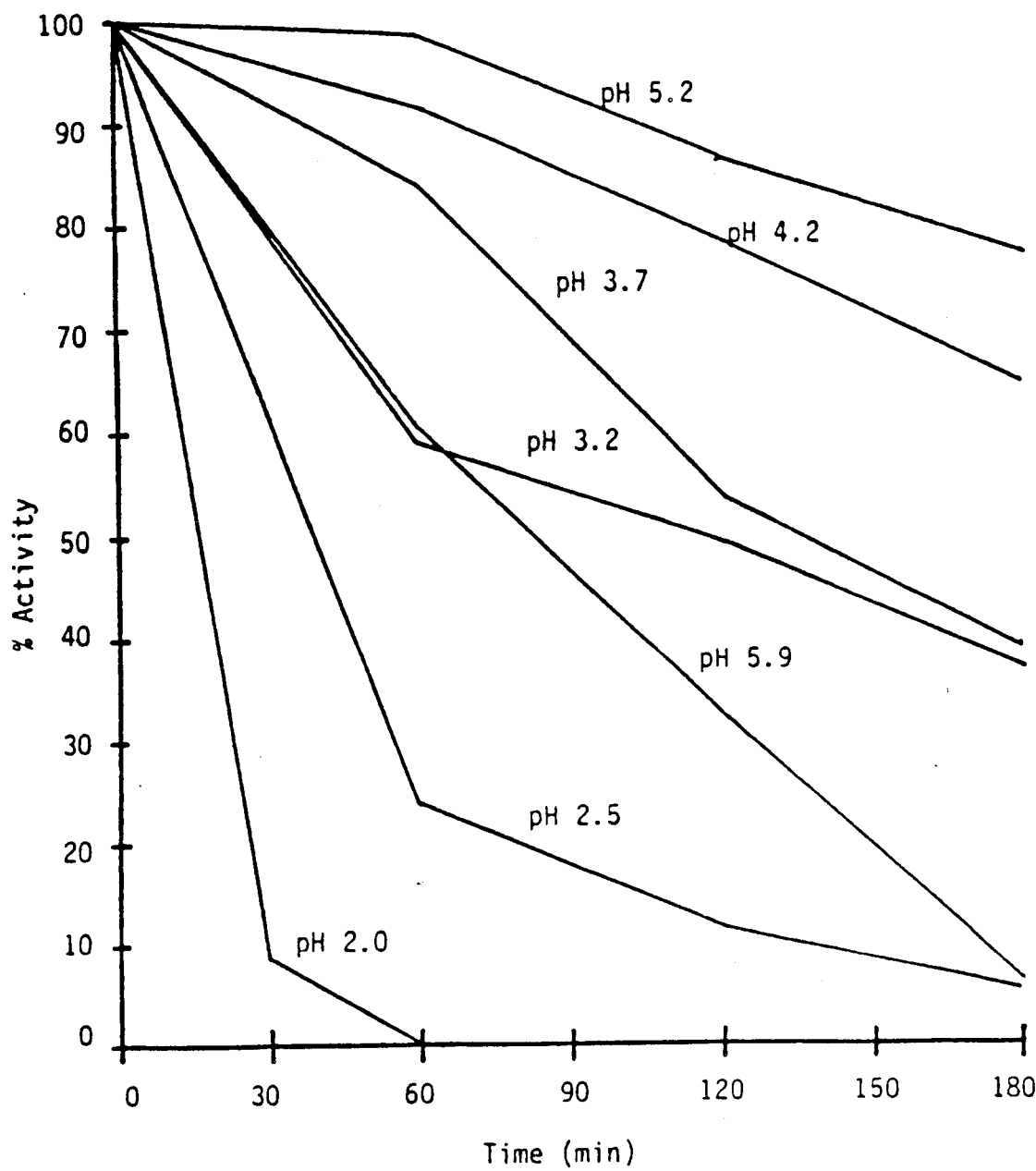
FIG.3 % Residual activity of P2.2 enzyme in acidified crude extracts incubated at 37°C for different time periods

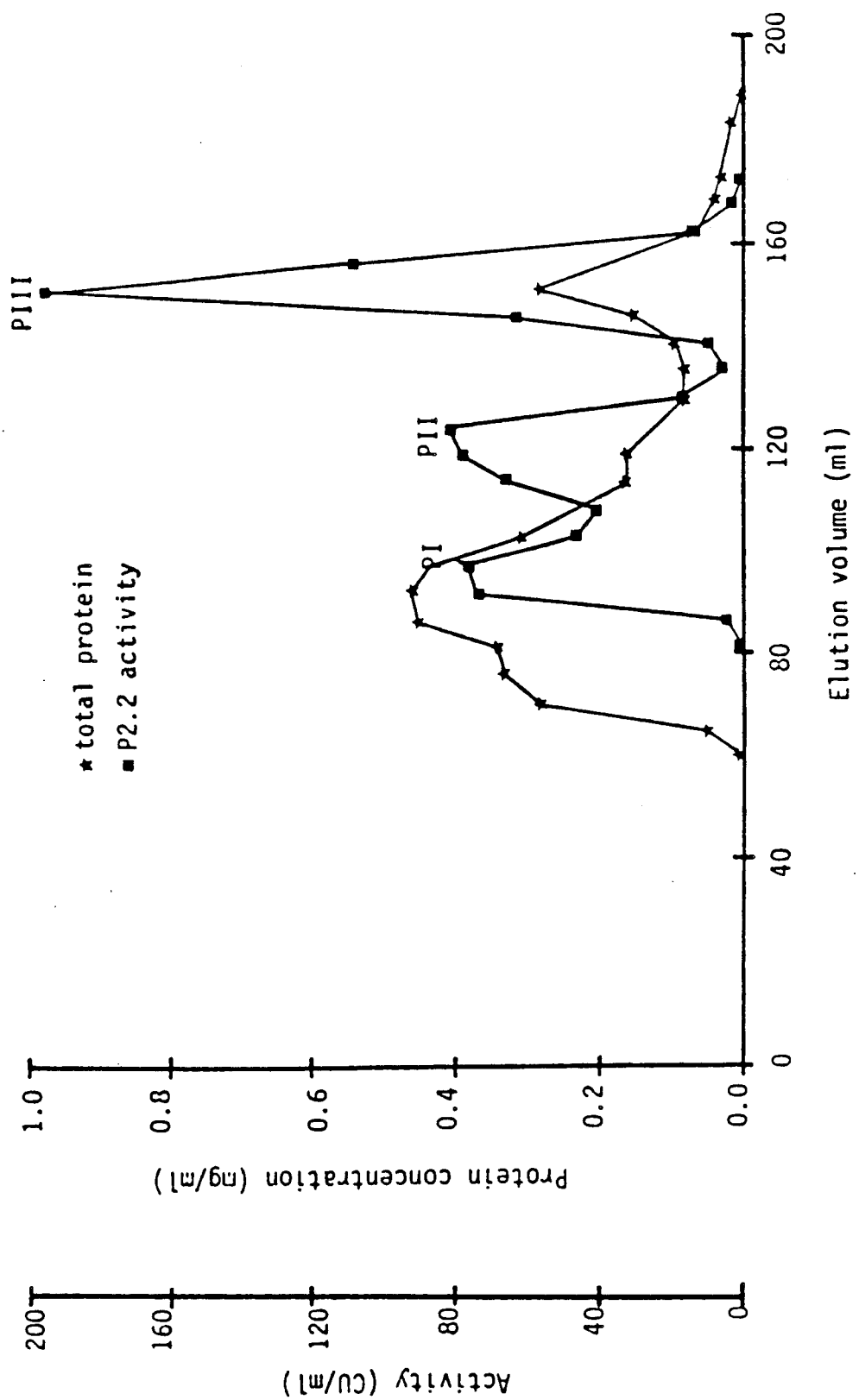
FIG. 4 Biogel p-150 gel filtration chromatogram of 40-70 % ethanol fraction from 25x ultrafiltration concentrate

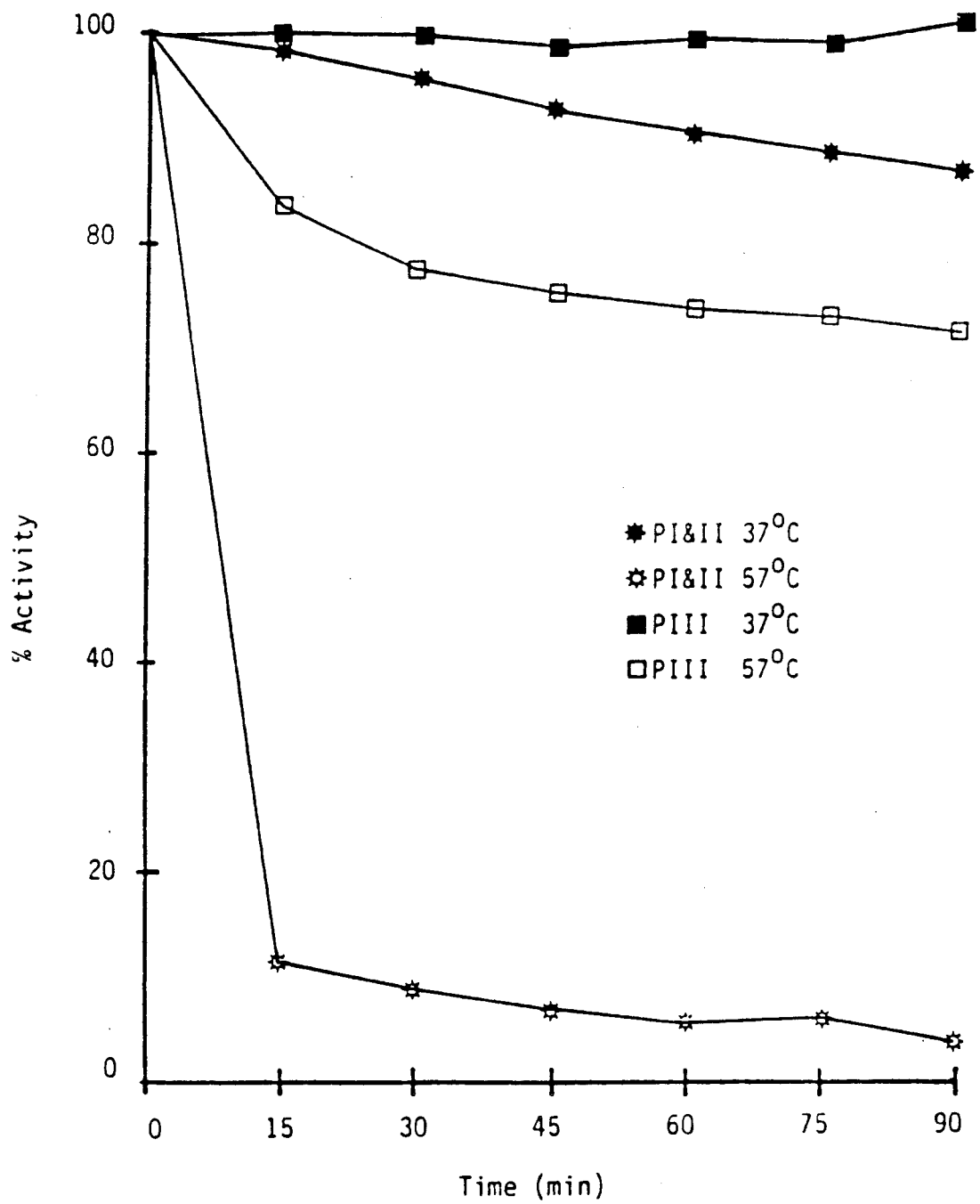
FIG. 5 Thermostability curves of purified PI&II and PIII

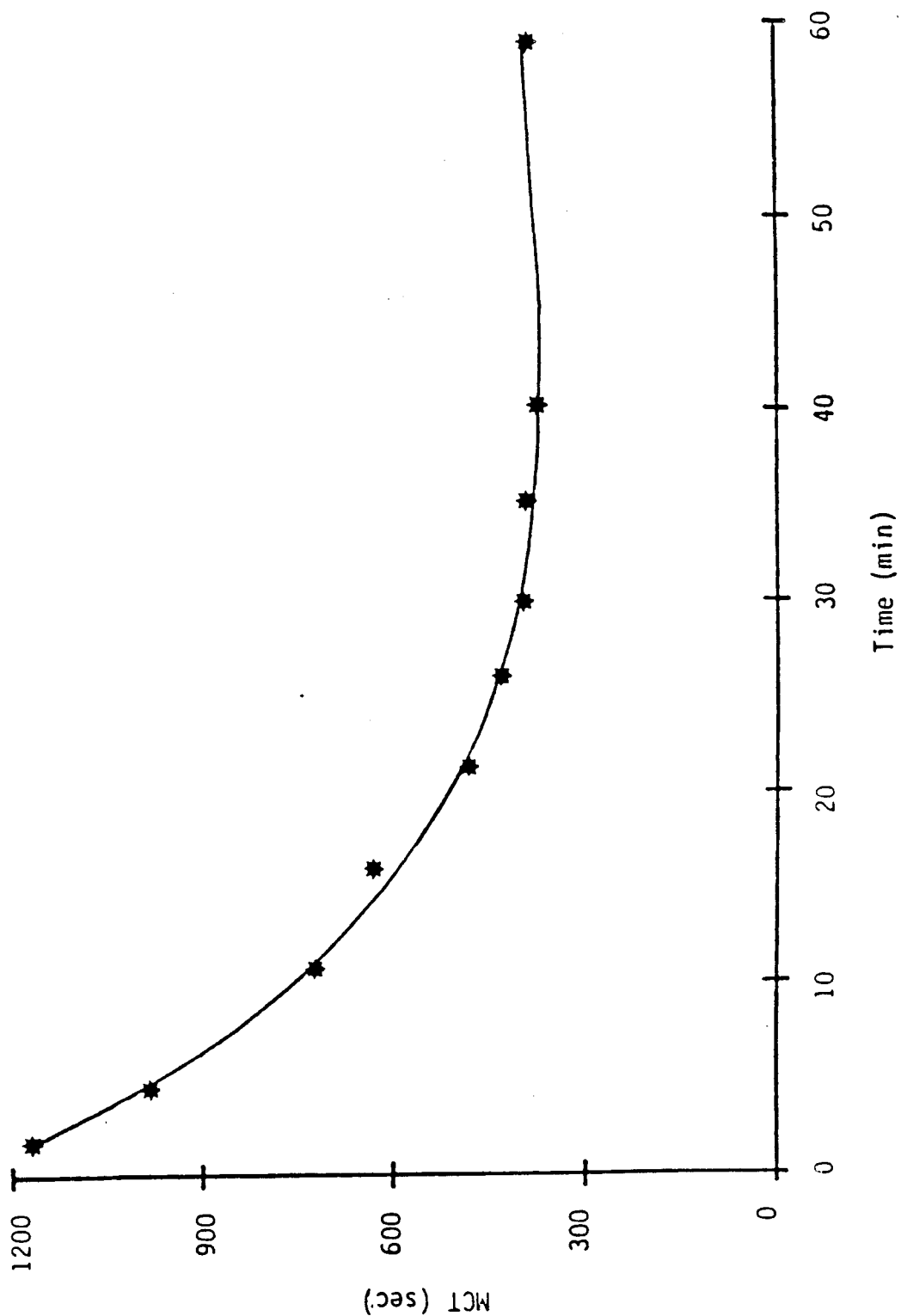
FIG. 6 Time course of activation of newly prepared clam rennet as indicated by the reduction of milk clotting time (MCT).

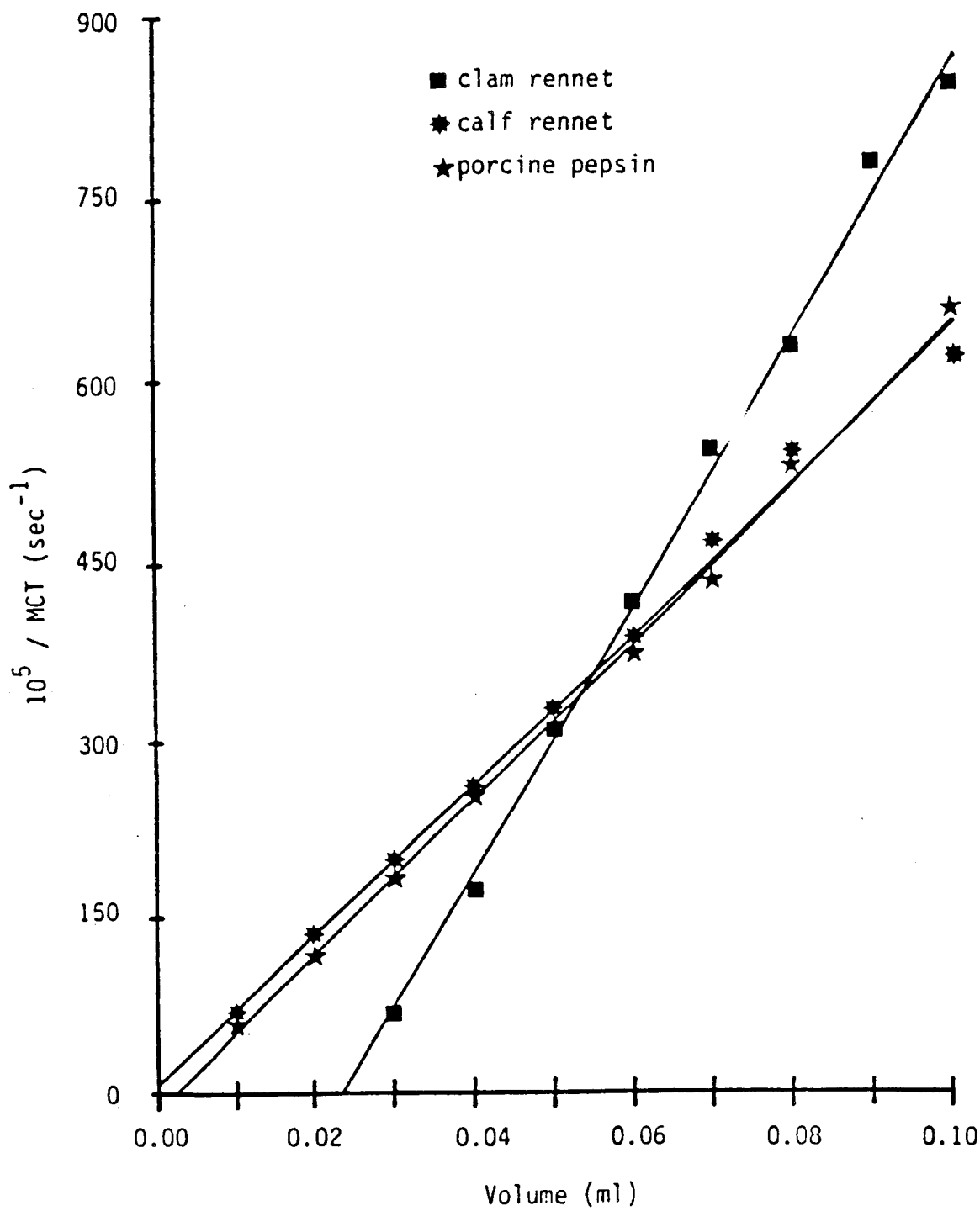
FIG. 7 Linear regression of milk clotting rate (1/MCT) against coagulant quantity

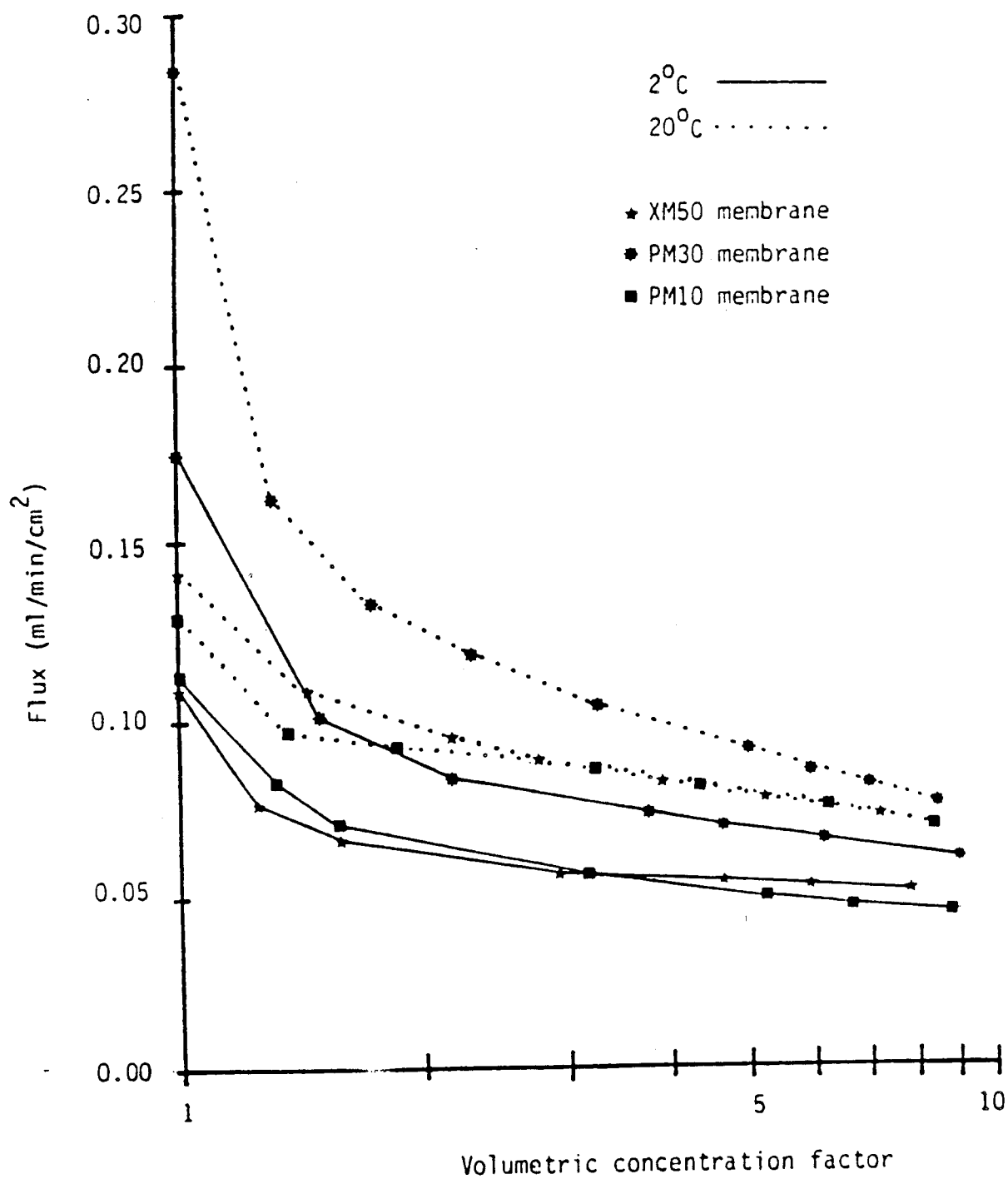
FIG. 8 The effect of membrane and temperature on the ultra-filtration flux of acidified clam viscera extract

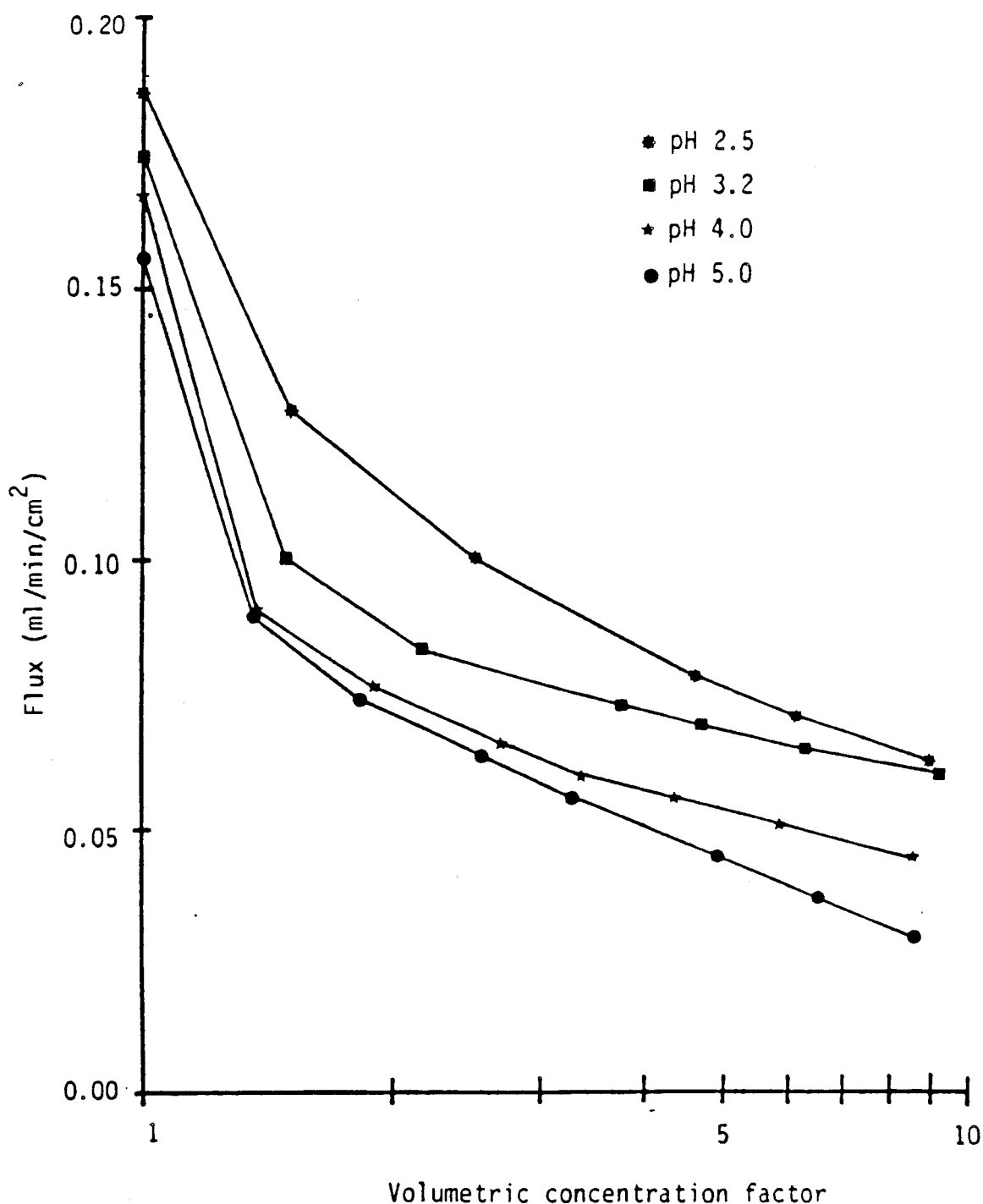
FIG. 9 The effect of pH on the ultrafiltration flux of acidified clam viscera extract

CLAM DERIVED PROTEINASES

GOVERNMENTAL RIGHTS

The invention described and claimed herein was made at least in part using funds of the New York Sea Grant Institute, Grant No. 344-5126-6 which includes funding through the National Oceanic and Atmospheric Administration, thus creating certain rights in the Federal Government in accordance with OMB Circular No. A-124.

BACKGROUND OF THE INVENTION

The surf clam, Spisula solidissima, is one of the relatively new seafood resources of the Atlantic coast shellfish processing industry. The major industry growth occurred in the mid 1940's and in 1958, when new offshore beds near Long Island were discovered (Zall et al., 1976, Pro. 7th Natl. Sympos. Food Processing Wastes, Environmental Protect. Series EPA-6002-76-304, Dec. 1, 1942). Today annual amounts of surf clam meats from New York approximate 2,000 metric tons of finished product or about 7% of the total landing of this clam in the United States.

Clam processing consists mainly of shucking, washing, mincing and canning or freezing of the meat. An appreciable amount of wastes, including clam wash water, bellies and shells are generated along with the clam meat in the processing line. Growing public environmental concern has stimulated research to improve the handling and disposal of these wastes. Hood, Zall and Conway (1976, supra) developed a process now being used by the seafood industry to convert minced clam wash water into clam juice. Zall and Cho (1977, Trans. A.S.A.E., 20: 160) showed that additional 5% of meat material could be captured from shell waste m=by manually culling visible amounts of meat adhering to the shell.

The clam belly which constitutes from 7 to 25% of the total meat is currently underutilized and causes a disposal problem. With the support from the New York State Sea Grant Program, this study was initiated to upgrade the economic value of clam belly waste. One hypothesis was that the structure and function of enzymes in the clam might have evolved differently from those of microorganisms, plants or animals encountered terrestrially. Some clam enzymes might have special characteristics suitable for industrial use or be an interesting product for scientific applications. For example, Shallenberger and co-workers (1974, Experimentia, 30: 597) found that the greatest activity of carbohydrases in surf clam was 3)-$\beta$-D-glucanase (laminarinase, laminaranase) capable of hydrolyzing the marine polysaccharide laminarian to simple sugars such as laminarabiose and glucose.

Proteases are of increasing importance in industrial applications. The possible uses of proteases include leather-bating, laundry cleaning, silk-degumming, chillproofing of beer, meat tenderizing, cheese-making and the production of pharmaceuticals. Much information is currently available for the proteases found terrestrially in plant, microbes and animals. However, the select types of properties and functions of proteases which may be found in clams are still much unknown. The first goal of this study was to isolate and characterize dominant proteolytic enzymes which might be found in clam viscera, because only after some basic biochemical properties and functions of the enzymes are understood can scientists predict or put into place uses for novel enzymes discovered. The next goal was to selectively seek the application for defined enzymes on the basis of the acquired information. These objectives were realized and fulfilled during the course of this work: Two proteinases were isolated and characterized from clam processing waste. One was a mammalian cathepsin B-like enzyme. Some potential uses for these two enzymes in processing food were demonstrated, such as in making cheddar cheese and tenderizing meat.

Previous studies on the proteolytic enzymes of invertebrates have focused on the enzymes active primarily at neutral or alkaline pH. Bundy and Gustafson (1973, Compar. Biochem. & Physiol., 44B: 241) purified a trypsin-like protease from the starfish. Trypsin and a low molecular weight protease had been isolated from the cardia fluid of crayfish (Zwilling and Neurath, 1981, Methods in Enzymology, 80: 633). Kozlovskaya and Voskovsky (1970, Compar. Biochem. & Physiol., 34: 137) surveyed a variety of marine invertebrates, including 14 bivalves, for alkaline proteases. A range of results from zero to low activity were obtained for the bivalves. Reid and Rauchert (1970, Comp. Biochem. & Physiol., 35: 689) demonstrated that tryptic and cymotryptic endopeptidases, carboxypeptidases A and B, and leucine aminopeptidase were present in the gastric juice and diverticula extract of Chlamys hericius. Similar results were obtained from several bivalve species (Reid and Rauchert, 1972, Comp. Biochem. & Physiol., 41A: 887) and two univalve species (Cockburn and Reid, 1980, Comp. Biochem. & Physiol., 65: 275). Although the latter investigations concentrated on alkaline endopeptidases from bivalves, it was traditionally realized that the greater portion of protein digestion occurred intracellularly at acid pH levels in the digestive diverticula, under the influence of enzymes about whose characteristics very little was known. Reid and Rauchert (1976, Comp. Biochem. & Physiol., 54B: 467) found that the intracellular proteolytic activity of the digestive diverticula in Tresus capax was approximately four times that of the stomach and acid proteinases are the most important enzymes. The acid endopeptidases have similar characteristics to vertebrate cathepsin B and D. Cathepsin B diminishes in winter when there is little food available while cathepsin D persists. This observation suggested that cathepsin B has a digestive role, and cathepsin D probably has a primary role, such as turnover of tissue protein which is non-digestive. Two acid exopeptidases, cathepsin A and C, are also present in the digestive diverticula. Surprisingly, two cooper-activated acid proteinases were isolated and crystallized from their zymogen forms of a sea mussel, Mytilus galloprovincialis (Dumitru et al., 1977, Revue Roumaine de Biochim., 14: 95; Dumitru et al., 1978, Comp. Biochem. & Physiol., 59B: 81; Iordachescu et al., 1978, Comp. Biochem. & Physiol., 61B: 119).

The fact that all the studies on molluscans have been limited to the digestive organs has led Aikawa and Aikawa (1982, Biochem. Systematics & Ecology, 10: 175) to investigate the distribution of the lysosomal acid proteinases in the tissues relating to various other functions distinct from nutrition. In 12 molluscans surveyed they found that cathepsin D-type proteinases with an optimum pH around 3 were predominant in various tissues, such as adductor muscle, foot, gill, mantle and midgut gland.

DESCRIPTION OF THE INVENTION

This invention relates to three enzymes, their isolation from the viscera of bivalves e.g. the surf clam, *Spisula solidissima* and the cherrystone clam, *Mercenaria mercenaria*, their characterization and uses thereof.

A relatively simple scheme to obtain relatively pure enzyme fractions comprises water extraction of bivalve viscera, acidification of the aqueous extract, stabilization of the aqueous extract with stabilizing amounts of chelating and reducing agents, e.g. cysteine and ethylenediaminetitraaceticacid (EDTA), concentrations for example by means of ultrafiltration and separation of the enzyme for example by ethanol fractionation and gel filtration.

The three enzymes (i.e. compositions having proteolytic activity) can be characterized as follows:

PI: A carboxyl proteinase enzyme, extractable from bivalve viscera, characterized as similar in activity to D-like mammalian cathepins and having a molecular weight of about 77,200 determined chromatographically against standard proteins, which enzyme is stable from pH 2.5 to pH 5.0 and has the following activities: optimum activity toward casein at pH 2.2 and hemoglobin at pH 2.5–2.8; insensitive to heavy metals; strongly inhibited by pepstatin; insensitive to inhibitors which commonly inhibit serine and thiol proteinases; insensitive to DNME in the presence of cupric ions: active against casein, bovine serum albumin and fibrinogen and substantial more active against hemoglobin as compared to the preceding; inactive against insoluble substrates collagen, elastin, fibrin; inactive against BAPNA.

PII: A carboxyl proteinase enzyme, extractable from bivalve viscera, characterized as similar in activity to D-like mammalian cathepins and having a molecular weight of about 36,700 determined chromatographically against standard proteins, which enzyme is stable from pH 2.5 to pH 5.0 and has the following activities: optimum activity toward casein at pH 2.2 and hemoglobin at pH 2.5–2.8: insensitive to heavy metals: strongly inhibited by pepstatin; insensitive to inhibitors which commonly inhibit serine and thiol proteinases; insensitive to DNME in the presence of cupric ions; active against casein, bovine serum albumin and fibrinogen and substantial more active against hemoglobin as compared to the preceding; inactive against insoluble substrates collagen, elastin, fibrin; inactive against BAPNA.

PIII: A thiol proteinase enzyme extractable from bivalve viscera, characterized as similar in activity to B-like mammalian cathepins and having a molecular weight of about 17,400 determined chromatographically against standard proteins, which enzyme is stable from pH 3.0 to pH 6.0 and has the following activities: optimum activity toward hemoglobin at pH 2.8 and toward casein at pH 2.8 and pH 5.5–5.8: sensitive to cupric ion and mercuric ion; slightly inhibited by $Pb^{++}$; sensitive to DNME in the presence of cupric ion; inhibited by PMSF, iodoacetamide, TPCK, TLCK and leupeptin, not inhibited by trypsin inhibitors, active against casein, bovine serum albumin and fibrinogen and substantially more active against hemoglobin compared to the preceding; inactive against insoluble substrates collagen, elastin, fibrin; active against BAPNA at pH 6.0–6.5.

The enzymes of this invention, especially PIII, are useful as substitutes for calf rennet for milk coagulation, for example in the production of cheese. The amount employed depends in part on the properties desired in the final product, e.g. a cheese. The enzymes of this invention can be employed in a cheese making process in milk coagulating amounts alone, or for example in combination with reduced amounts of other known coagulating agents. As shown hereinafter cheddar cheese of reasonable quality can be produced using the enzyme of the invention in a conventional cheesemaking process. It is noted that a faster ripening process resulted as compared to the use of calf rennet.

The enzymes of this invention, especially PIII, are useful to tenderize meat. The enzymes are employed as a postmortem treatment of meat by contacting the meat with the enzyme (usually in aqueous solution) in an amount and for f time sufficient to reduce the shear force necessary to cut the meat.

As employed herein "partially purified form" means separated from the parent bivalve tissue in which the enzymes naturally occur.

There follow a number of Examples which are to be considered illustrative rather than limiting. All parts and percentages are by weight unless otherwise specified. All temperatures are degrees centigrade.

EXAMPLE 1

1. Sources of Clam Bellies

Two shipments of frozen surf clam wastes (bellies), one in early April and the other in the late October, were obtained from a Long Island clam processing company. Fresh bellies were also obtained by manually shucking live cherrystone or surf clams purchased in a local food store in Ithaca, N.Y.

2. Crude Enzyme Extract

About 200–500 g of clam bellies were mixed with two times amount of chilled water and homogenized in a commercial Waring blender at high speed for 2 min. The homogenate was then centrifuged at 4° C. and 13,000×g for 30 min. The supernatant was used as a crude enzyme extract for further study.

3. pH Adjustment

During purification steps the pH of the enzyme preparation was adjusted by slow addition of 2 N HCl or NaOH with adequate mixing.

4. Ammonium Sulfate or Ethanol Fractionation

Ammonium sulfate frationation was carried out by dissolving the chemical to desired degree of saturation over a period of 20 min 100 ml of water can be saturated by 72 g of ammonium sulfate at 20° C. Ethanol fraction was carried out by slowly mixing 95% or 100% alcohol with enzyme extract to desired volume percentage of alcohol in the mixture. These mixtures were then centrifuged at 4° C. and 13,000×g for 10 min to separate the supernatant and precipitates.

5. Ultrafiltration

Concentration and partial purification of enzyme extract was carried out in a TCF-10 batch ultrafiltration unit (Amicon Co., Lexington, MA) installed in a 2° C. walk-in cold room. XM-50 membranes, which have a nominal molecular-weight-cut-off (MWCO) of 50,000, were used throughout the purification and characterization part of this study. The unit was operated at 35 psig with a recirculation rate of 200 ml/min. Pressure was provided by compressed nitrogen.

6. Gel Filtration Chromatography

Two to three milliliters of active enzyme fraction were chromatographed on a Sephadex G-200 or Biogel p-150 column (2.2×75 cm) pre-equilibrated with elution buffer. Each 5.4 ml was fractionated at room temperature for protein concentration and proteolytic activity determinations. To estimate the molecular weights of the proteinases the column was calibrated by eluting mixtures of standard proteins under same conditions. The standard proteins, including thyroglobulin (M.W. 670,000), gamma-globulin (M.W. 158,000), ovalbumin (M.W. 44,000), myoglobin (M.W. 17,000) and vitamin B12 (M.W. 1,350), were obtained in mixture from Bio-Rad Laboratories (Richmond, CA).

7. SDS Polyacrylamide Gel Electrophoresis

The fraction from each purification step was dialyzed and lyophilized for use in electrophoresis. Sample preparation and SDS (sodium dodecyl sulfate) polyacrylamide gel electrophoresis were carried out according to the method described by Weber and Osborn (1969) *J. Biological Chem.*, 244: 4406, except that 2-mercaptoethanol was omitted from sample preparation.

8. Proteolytic Activity Determination

The activity of proteolytic enzymes was measured by Anson's method (1938) *J. Gen. Physiology*, 22: 79, or Kunitz's method (1947) *J. Gen. Physiology*, 30: 291 with modifications.

a. Substrates 2.5 g of purified casein or 5.0 g of bovine hemoglobin, both from Sigma Co. (St. Louis, MO), was dissolved in 100 ml of hot 0.015 n HCl and diluted to 250 ml to make 1% casein or 2% hemoglobin solution.

b. Buffers

HCl-KCl, citrate-phosphate and Tris-HCl buffers were used for pH in the range from 1.3 to 1.9, 1.9 to 7.0 and 7.0 to 10.0, respectively. Buffers were prepared by mixing 0.2 M solution of each reagent pair to predetermined pH.

c. Assay Procedure

To 0.05–0.25 ml enzyme solution was added 1.95–1.75 ml buffer solution, followed by 1 ml of substrate. The mixture was incubated at 37° C. for 15 min before the addition of 5 ml of 0.2 M Trichloroacetic acid (TCA) to precipitate undigested protein. After another 10 min, the mixture was filtered through Whatman No. 42 paper. The amount of TCA soluble peptides resulted from enzymatic digestion was measured spectrophotometrically at $A_{280}$. A blank was run simultaneously with each determination by reversing the addition order of substrate and TCA.

d. Definition of Activity Units

The activity of proteolytic enzymes was expressed in casein unit (CU) or hemoglobin unit (HU). One CU or HU was arbitrarily defined as 0.001/min. increase in $A_{280}$ under assay conditions using casein or hemoglobin as substrate, respectively.

9. Protein Concentration Determination

Concentration of protein in each enzyme preparation was measured on the basis of dye-binding assay developed by Bradford (1976) as described in the Bio-Rad protein standard assay bulletin (Bio-Rad Instruction Manual 82-0275-1282). To 0.1 ml of properly diluted protein solution was added 5 ml of 1:4 diluted dye reagent (Comassie Brilliant Blue G-250). After 15 min the color developed was measured spectrophtometrically at $A_{595}$ against reagent blank. The protein concentration was then read from the standard curve prepared by bovine gamma-globulin solution. The protein concentration in the eluate from gel filtration can also be determined by the absorbence at 280 nm using same standard reference. This method agreed well with dye-binding method.

10. Evidencing the Existence of Proteinases a. pH-Activity Profile of Crude Extract from Fresh Clam Viscera

A scanning of proteolytic activity over pH range from 1.5 to 9.0 was conducted to locate the pH optima of various proteolytic enzymes in the crude extract of fresh surf clams. Three distinct activity peaks were found to be at pH 2.2, 5.5 and 7.6 when casein was used as substrate. These three peaks were designated, respectively, as P2.2, P5.5 and P7.6 for the sake of convenient reference. However, only two activity peaks occurred when hemoglobin was used as substrate, one being at pH 2.8 and another at pH 7.6. In general the pH optimum is not a characteristic of the enzyme alone but is also strongly related to the nature and conformation of the substrate or the enzyme-substrate complex. For example, denaturation of hemoglobin and serum albumin shifts the pH optimum of their susceptibility towards pepsin action from 2 to 3.5 (Schlamowitz and Peterson, 1959, *J. Biological Chem.*, 234: 3137). The position of the pH optimum may also be influenced by the ionic strength of the medium (Douzou and Maurel, 1977, *Pro. Nat. Acad. Sci. U.S.A.*, 74: 1013). Casein was more readily degraded at high pH and the reverse seemed to hold for hemoglobin.

Similar results were obtained for the extract from fresh cherrystone clams. Surf clam (*Spisula solidissima*) and cherrystone clam (*Mercenaria mercenaria*) are different species, but they seem to have similar pH-activity relationship. This observation agrees with the conclusion drawn from a literature survey of the proteolytic enzymes in bivalves (Reid, 1976, *The Veliger*, 20: 260). The conclusion was that low pH (2–3.5), intermediate pH (4–6.5) and high pH (7–8) proteolytic enzymes occurred universally in this class of mollusca. Surf clam appeared to have sightly higher proteolytic level than cherrystone clam.

b. Distribution of Proteinases

Various proteolytic activity has been reported both in the muscle tissue of both mammals and clams. Table 1 shows that clam meat has very little activity as compared to the viscera extract under the three peak pHs found in the viscera extract.

TABLE 1

Proteolytic levels of clam meat and viscera

| Source | Protein conc. (mg/ml) | Activity (CU/ml) P2.2 | P5.5 | P7.6 |
|---|---|---|---|---|
| Meat | 16.08 | 2.7 | 4.0 | 0.0 |
| Viscera | 7.60 | 162.7 | 300.0 | 220.0 | c. Separation of Proteinases by Sephadex G-200

Crude extract with a pH of 6.4 from fresh cherrystones was fractionated by ammonium sulfate to remove viscous material. The fraction of 45-75% ammonium sulfate saturation, which retained most of the proteolytic activity of P2.2, P5.5 and P7.6, was chromatographed on Sephadex G-200 column and eluted with 0.05M citrate-phosphate buffer at pH 6.4. The main portion of the protein together with P7.6 activity emerged at the very early fraction. P2.2 activity appeared separately at a much later fraction. However, P5.5 activity was eluted from two fractions which coincided with P7.6 and P2.2 fractions. This observation suggests that P5.5 activity might be a pseudo peak created by some synergistic action of P2.2 and P7.6 in the region of overlap within their pH-activity profiles. Another possibility is that P5.5 enzyme itself might have been inactivated through the gel filtration process. The molecular weights of P2.2 and P7.6 enzymes were estimated from the column calibrated with proteins of known molecular weights. From gel filtration theory the plot of logarithm of the molecular weight versus the ratio of elution volume (Ve) and void volume (Vo) of the column yields a straight line. As shown in FIG. 1 the molecular weights of P2.2 and P7.6, respectively, were estimated to be 73,000 and 718,000 by intrapolating from the regression line which was established by proteins of known molecular weights.

d. pH-Activity Profile of Crude Extract from Clam Processing Waste

The relationship between pH and activity of crude extract prepared from surf clam processing waste is shown in FIG. 2. Similar results were observed from clam waste obtained in the fall, except that the proteolytic level was only about two-thirds of the levels found in spring samples. The loss of P7.6 activity leads one to suspect that this enzyme is inherently unstable during frozen storage or is inactivated by the heat or hot water treatment in the clam processing. The relative levels of activity of P2.2 and P5.5 in clam waste are also different from that of fresh clam. P5.5 activity was relatively low in the clam waste. This observation further suggests that at least part of the P5.5 activity is contributed by the P7.6 enzyme. Thus, lower P5.5 activity was observed when P7.6 activity had been lost from the waste. However, it was still not apparent whether P5.5 activity is a distinct enzyme or there is just one enzyme with two activity peaks toward casein, the latter being an artifact resulting from the low solubility of casein near its isoelectric point of pH 4.6. All further efforts were aimed to recover and utilize the P2.2 enzyme from clam waste since the recovery of useful products from clam processing waste was a cardinal goal of this study.

11. Developments in Purification Methodology a. Extraction

The simple autolysis method was investigated to optimize the yield of enzymes from clam waste. Autolysis was conducted at temperature range from 2°-45° C., pH range from 2.5-6.0 and sodium chloride concentration from 0-7.5% for 0-24 hours. None of the conditions had produced any significant increase of total activity as compared to simple water extraction.

b. Acidification

Acidification has an advantage in purifying enzymes with low pH optimum due to their greater stability at lower pH. The effect of acidification of crude extract to different pHs is shown in Table 2. At pH above 3.2 the protein concentration decreased with decreasing pH without jeopardizing the P2.2 activity. As pH was further reduced, loss of activity occurred and protein concentration increased slightly. The increase in protein concentration was likely due to the resolubilization of some proteins at low pH.

TABLE 2

Acidification effect on the purification of P2.2

| pH | Protein (mg/ml) | Activity (CU/ml) | Activity (CU/mg) | Purity factor | Yield (%) |
|---|---|---|---|---|---|
| 5.9* | 7.82 | 132.0 | 16.88 | 1.00 | 100.0 |
| 5.2 | 4.28 | 136.7 | 31.94 | 1.89 | 103.6 |
| 4.2 | 2.45 | 131.3 | 53.59 | 3.17 | 99.5 |
| 3.7 | 2.06 | 130.0 | 63.11 | 3.74 | 98.5 |
| 3.2 | 1.72 | 133.3 | 77.50 | 4.59 | 101.0 |
| 2.5 | 1.82 | 123.3 | 67.75 | 4.01 | 93.4 |
| 2.0 | 1.98 | 100.7 | 50.86 | 3.01 | 76.3 |

*pH of the crude extract from clam processing waste

The stability of a crude enzyme preparation is one of the most important factors affecting the purification result. FIG. 3 shows the stability of P2.2 enzyme in the extracts acidified to different pHs. P2.2 activity was most stable at pH between 4.2 to 5.2, but it was not so stable at pH 3.2 which gave maximum purification effect. Thus, intuitively the logic is to acidify the crude extract to pH 3.2, then adjust pH back to a value between 4.2 and 5.2 as soon as possible after separation of precipitates.

c. Stabilization with Reducing and Chelating Agents

In addition to the chelating agent, EDTA, several reducing agents were added to the acidified extract and pH adjusted to 5.0. The effect of these reagents on P2.2 stability is shown in Table 3. All reducing agents and EDTA stabilized P2.2 activity to some degree. Cysteine-HCl was the most effective and slight activation by this compound was also observed in the initial stage. These observations suggest that the mechanism involved in the inactivation of P2.2 enzyme includes oxidation process which might be catalyzed by heavy metals, and P2.2 activity might involve the enzyme with thiol (-SH) group as an active site.

TABLE 3

Retention of P2.2 activity pre-incubated with chelating and reducing agents at 37° C. and pH 5.0

| Reagent (0.01 M) | Time (hours) 0 | 1 | 2 | 3 | 20 |
|---|---|---|---|---|---|
| Control | 100.0 | 89.6 | 73.8 | 57.9 | 39.6 |
| Cysteine-HCl | 105.5 | 113.4 | 118.3 | 112.8 | 90.9 |
| Na$_2$—EDTA | 101.8 | 92.1 | 83.5 | 76.2 | 64.4 |
| Ascorbic acid | 98.8 | 101.2 | 101.8 | 98.2 | 62.2 |
| Hydrazine sulfate | 98.8 | 81.7 | 66.5 | 64.0 | 56.1 |
| 2-mercaptoethanol | 95.7 | 102.5 | 91.4 | 94.4 | 67.3 |

Plant proteases such as papain (Arnon, 1970, *Methods in Enzymology*, 19: 226), Bromelain (Murachi, 1970,

*Methods in Enzymology*, 19: 273) and Ficin (Liener and Friedenson, 1970, *Methods in Enzymology*, 19: 261), microbial proteases from *Streptococcus* (Elliot and Liu, 1970, *Methods in Enzymology*, 19: 252) and *Aspergillus* (El-Zalaki et al., 1974, *Alex. J. Agric. Res.*, 22: 63), and several cathepsins (Barrett and Kirschke, 1981, *Methods in Enzymology*, 80: 535), from animal tissue extracts are thiol proteinases with this typical property. The stimulation effect of cysteine on the proteolytic activity in the crude extract from bivalves has also been observed by Rosen (1949, *Archiv. Kemi*, 1: 205) and Reid and Rauchert (1970, *Compar. Biochem. and Physiol.*, 35: 689). An implication is that P2.2 enzyme might be the same type of enzyme investigated by these investigators.

Optimum activation of the thiol enzyme was found to occur upon simultaneous application of a thiol compound, like cysteine or thioglycolate, and a heavy metal-binding reagent like EDTA (Kimmel and Smith, 1954, *J. Biological Chem.*, 207: 515). The synergistic effect of EDTA and cysteine was investigated. The optimum concentration for EDTA or cysteine alone is 10 mM and 2.5 mM, respectively. Slight inactivation was observed at low cysteine concentration. This phenomenum has also been observed in some thiol proteinases (Sluyterman, 1967, *Biochem. Biophys. Acta*, 139-430). It is noted that cysteine and EDTA are synergistic. With the addition of 2.5 mM EDTA the stability of P2.2 enzyme increased significantly over the entire concentration range of cysteine from 0 to 10mM.

d. Ethanol Fractionation

Fractionation of proteinaceous material is generally achieved by salts and/or organic solvents. Ammonium sulfate is the most popular salt and ethanol is a most desirable solvent. Preliminary tests suggested that ethanol is better than ammonium sulfate in fractionating P2.2 enzyme, because the ethanol fractionation provided higher yield and purification factor. Thus, the ethanol fractionation method was adopted as a next step to purify P2.2 enzyme from an acidified-stabilized extract. The distribution of proteins and P2.2 activity in different ethanol fractions is shown in Table 4. No significant activity could be detected in both 0–40 and 70–100% ethanol fractions. The 60–70% ethanol fraction had the highest purity. However, a 40–70% ethanol fraction is most desirable because it achieved more than two folds of purication without sacrificing much of the activity.

TABLE 4

Ethanol fractionation of acidified-stabilized extract

| Ethanol (% v/v) | Protein (mg/ml) | Activity (CU/ml) | Activity (CU/mg) | Purity factor | Yield (%) |
|---|---|---|---|---|---|
| Control | 1.62 | 119.6 | 73.8 | 1.00 | 100.0 |
| 40–50 | 0.20 | 1.2 | 6.0 | 0.08 | 1.0 |
| 50–60 | 0.28 | 24.5 | 87.5 | 1.19 | 20.5 |
| 60–70 | 0.13 | 52.2 | 401.5 | 5.44 | 43.6 |
| 50–70 | 0.41 | 85.6 | 208.8 | 2.83 | 71.6 |
| 40–70 | 0.61 | 97.3 | 159.5 | 2.16 | 81.4 | e. Ultrafiltration

The fractionation process of crude enzyme preparation in dilute form might not be feasible in commercial application due to the large capital investment and operational cost required to handle huge amounts of fluid and the need to purchase expensive salts or solvents. Thus, it appears necessary to reduce the volume of crude enzyme preparations through a concentration process before further processing. Ultrafiltration process is probably the best choice currently available for concentrating enzyme solutions, because the process is gentle and non-destructive to most enzymes. Furthermore, partial purification can be simultaneously achieved during concentration. Table 5 shows the effect of different degree of concentration by ultrafiltration. The decrease in yield with increasing concentration factor is anticipated because more leakage of enzyme into filtrate occurs as the driving force (enzyme concentration) in the retentate increases.

TABLE 5

The effect of ultrafiltration on the activity of P2.2

| Conc. Factor | Volume (ml) | Protein (mg/ml) | Activity (CU/ml) | Activity (CU/mg) | Purity factor | Yield (%) |
|---|---|---|---|---|---|---|
| 1 | 500 | 1.69 | 145.3 | 86.0 | 1.00 | 100.0 |
| 2 | 250 | 2.87 | 280.0 | 97.6 | 1.14 | 96.4 |
| 5 | 100 | 6.73 | 710.0 | 105.5 | 1.23 | 97.7 |
| 10 | 50 | 12.61 | 1373.3 | 108.9 | 1.27 | 94.5 |
| 25 | 20 | 28.82 | 3383.3 | 117.4 | 1.37 | 93.1 |

Although the purity of the enzyme increases only slightly, it should be pointed out that the measurement of purity is based totally on the concentration of protein. The total solids content of the retentate is only about 2 times of the original extract even with 25-fold concentration. The large amount of low molecular weight solubles removed from the filtrate is not included in the purity parameter. Nonetheless, the most important function of ultrafiltration is the reduction of volume. Further reduction in volume might still be possible, but the minimum operating volume of the TCF-10 batch system prohibited further investigation.

f. Biogel p-150 Gel Chromatography

Sephadex G-200 (fractionation range 5,000–600,000) used in previous study was replaced by Biogel p-150 (fractionation range 15,000–150,000) to purify P2.2 enzyme, because the estimated molecular weight of P2.2 from Sephadex G-200 column suggested that a column with lower and narrower fractionation range might give better separation. The 40–70% ethanol fraction from 25-fold retentate was applied to Biogel p-150 column and eluted with 0.05M citrate-phosphate buffer containing 10 mM cysteine and 2.5 mM EDTA, the pH being 4.2. FIG. 4 shows that three P2.2 peaks emerges from the column. The most active fractions of each peak were collected for further investigation. For convenient reference these three peaks were designated as PI, PII and PIII. The observation of three P2.2 peaks was surprising, since only one P2.2 activity peak was observed from Sephadex G-200 column. One of the possible reasons is that Biogel p-150 has a fractionation range more suitable for molecules of close molecular weights. Another possibility is that one or two of these enzymes might have been inactivated during Sephadex G-200 chromatography, since no cysteine and EDTA were added to stabilize the enzymes. From their elution volumes, the molecular weights of PI, PII and PIII were, respectively, estimated to be 77,200, 36,700 and 17,400.

g. Purity of Three P2.2 Components

The homogenity of PI, PII and PIII was investigated by SDS polyacrylamide gel electrophoresis. PIII appeared as a single band at a position corresponding to the estimated molecular weight. Besides the major bands corresponding to the molecular weights of PI and PII, several faint bands of lower molecular weights also appeared from PI and PII fractions. These low molecular weight bands might be the autolysis products of the enzymes or the subunits disassociated by SDS, or impurities. Nonetheless, the distinct separation of these three peaks by gel filtration warranted the characterization of these enzymes.

h. Conclusions

The predominant proteinases in the viscera of clams are of neutral (P7.6) and acid (P2.2) types. Neutral proteinase appears unstable and could not be recovered from clam waste. A simple scheme has been developed to obtain three relatively pure P2.2 components. The scheme includes water extraction, acidification, stabilization with cysteine and EDTA, ultrafiltration, ethanol fractionation and gel filtration.

EXAMPLE 2

Characterization and Identification of Purified Proteinases

Introduction

Unlike other groups of enzymes, the identity of the proteinases isolated from a new source can not simply be recognized by their specific activity against substrates, because proteinase specificity is so complex that it can not form the basis of a useful identification system. However, it is possible to classify the proteinases into different catalytic groups by the application of activators or inhibitors which react specifically with the essential catalytic sites of the enzymes. The group identity supplemented with physico-chemical properties of the enzyme, such as molecular weight, substrate specificity and pH and temperature profiles, would enable one to further understand the nature of the proteinases.

1. Use of Inhibitors in the Classification of Proteinases

Since no satisfactory scheme for the classification of proteinases seems possible on the basis of specificity, the identity of the essential catalytic group of the enzyme is used to create the four classes of 'serine', 'thiol', 'carboxyl' and 'metallo' proteinases as was first done by Hartley (1960, Annual Rev. Biochem., 29: 132). These are the categories 3.4.21, 3.4.22, 3.4.23 and 3.4.24, respectively of the IUPAC-IUB Enzyme Nomenclature List (1972). A fifth category, 3.499, which has been termed the 'waiting list', is available for proteinases of undefined catalytic class. Because inhibitors are more useful than substrates in determining the chemical nature of the catalytic groups, they have acquired special importance in the classification of proteinases. Few of the available inhibitors are sufficiently effective and specific to allow clear cut decisions in every case. Nevertheless, a simple scheme has been drawn up as a general guide (Barrett, 1977a, *Proteinases in Mammalian Cells and Tissues*, Barrett ed. North-Holland Pub. Co., Amsterdam, p. 1). The scheme is shown in the Table 6. The majority of proteinases would be satisfactorily categorized by application of the criteria indicated in the table. Those tests should preferably be used in conjunction with more detailed information to be found elsewhere in the literature.

TABLE 6

The assignment of a newly discovered endopeptidase to a catalytic class

| Inhibitor (preincubation at 20° C. for 1 hr | Class of endopeptidase | | | |
|---|---|---|---|---|
| | Serine | Thiol | Carboxyl | Metallo |
| Pepstatin(1 ug/ml) | — | — | Inhibited | — |
| Dithiothreitol + EDTA (each 2 mM) | — | Activated | — | Inhibited |
| DPF or PMSF (1 mM) | Inhibited | (Inhibited) | — | — |
| Lima bean or soybean trypsin inhibitor (100 ug/ml) | Inhibited | — | — | — |
| 1,10-Phenanthroline (1 mM) | — | — | — | Inhibited |
| 4-Chloromercuri-benzoate (1 mM) | — | Inhibited | — | — |
| Diazoacetylnorleucine methyl ester + $Cu^{2+}$ (each 1 mM) | — | Inhibited | Inhibited | — |
| Expected pH optimum | 7–9 | 4–7 | 2–5 | 7–9 |

2. Select Properties of Proteinases of Viscera Origins

Most of the proteinases isolated from viscera have been of mammalian origin. Nonetheless, a survey of these proteinases would provide useful guides in evaluating the proteinases isolated from lower animals. Table 7 summarizes the catalytic category, molecular weight, optimum pH and general proteolytic activity of most of the important proteinases found in mammalian viscera tissues.

TABLE 7

Summary of select properties of proteinases from mammalian viscera tissues

| Category | Source | Molecular weight (× 1,000) | General proteolysis | Optimum pH | Reference |
|---|---|---|---|---|---|
| Serine | | | | | |
| Trypsin | pancreas | 22–26 | +++ | ~8.0 | Walsh, 1970 |
| Chymotrypsin | pancreas | 25–29 | +++ | ~8.0 | Wilcox, 1970 |
| Cathepsin G | spleen | 23–30 | ++ | ~7.5 | Barrett, 1981 |
| Kallikrein | pancreas kidney | <30 | + | 8.6–8.8 | Geiger and Fritz, 1981 |
| Urokinase | kidney | 32, 55 | + | 7.5–7.6 | Christman et al., 1977 |
| Enterokinase | duodenum | 200–300 | ++ | 6–9 | Kenny, 1977 |
| Elastase | spleen | 27–30 | ++ | 8.2–8.5 | Starkey, 1977 |
| Thiol | | | | | |
| cathepsin B | spleen liver | 24–28 | ++ | 3.5–6.0 | Barrett and Kirschke, 1981 |
| cathepsin H | liver | .28 | + | 5–6 | same as above |
| cathepsin L | liver | 21–24 | +++ | 5.0–5.5 | same as above |
| Carboxyl | | | | | |
| Pepsin | stomach | 32–42 | +++ | 1.7–2.0 | Ryle, 1970 |

TABLE 7-continued
Summary of select properties of proteinases from mammalian viscera tissues

| Category | Source | Molecular weight (× 1,000) | General proteolysis | Optimum pH | Reference |
|---|---|---|---|---|---|
| Gastricin | stomach | 31–33 | +++ | 3.0 | Tang, 1970 |
| Chymosin | stomach | 31–36 | + | 3.5 | Foltmann, 1970 |
| Renin | kidney | ~42 | + | 5.5–8.0 | Barrett, 1977a |
| Cathepsin D | spleen | ~42 | ++ | 2.8–5.0 | Barrett, 1977c |
| Metallo NEKBB[a] | kidney | 87–96 | +++ | 6.0 | Kenny, 1977 |
| Unknown CAP[b] | muscle | 100–120 | +++ | 7–8 | Waxman, 1981 |

[a]Neutral endopeptidase of kidney brush border
[b]Calcium activated protease

3. Substrate Specificity of Proteinases

In general, each group of proteinasaes preferentially attacks substrates. Carboxyl proteinases, in which the hydrolysis of peptide bonds is catalyzed by two or more aspartyl groups (Tang, 1979, *Molecul. and Cellular Biochem*, 26: 93), are most likely to attack peptide bonds linking amino acids with hydrophobic side chains. For example, the most susceptible bonds of the oxidized B-chain of insulin to cathepsin D are leu-tyr, tyr-leu,, phe-phe and phe-tyr; clearly, each reaction involves markedly hydrophobic residues, at least one being aromatic (Barrett, 1977c, supra., p. 209). Thiol proteinases, whose catalytic sites involve a cysteine-histidine pair (Shipton, 1975 FEBS Letters, 250: 365), have very broad specificity toward both proteins and small molecular weight substances. For instances, papain and cathepsin B both cleave the oxidized B-chain of insulin at numerous places and attack small substrates (Arnon, 1970, *Methods in Enzymology*, 14: 226; Barrett, 1977b, supra p. 181). Serine proteinases, like trypsin and subtilisin, operate by analogous mechanisms involving specific seryl and histidyl residues (Walsh and Wilcox, 1970, *Methods in Enzymology*, 19: 31). The specificity of trypsin is directed toward lysyl and arginyl residues and the specificity of subtilisin is directed toward leu-tyr in the oxidized B-chain of insulin (Morihara and Tsuzuki, *Arch. Biochem. and Biophysics*, 129: 620).

4. Purified PI, PII and PIII

PI, PII and PIII were purified by the optimum scheme developed in Example 1. Crude extract was first acidified to pH 3.2, and after the removal of precipitates by centrifugation the acidified extract was stabilized by addition of 10 mM cysteine-HCl, 2.5 mM EDTA. The pH was then adjusted back to 4.2. 500 ml of acidified-stabilized extract was concentrated 25-fold by ultrafiltration, followed by ethanol fractionation and gel filtration. The 40–70% ethanol fraction was applied to Biogel p-150 column and eluted with 0.05M citrate-phosphate buffer containing 10 mM cysteine-HCl and 2.5 mM EDTA at pH 4.2. The PI, PII and PIII fractions were collected and frozen at −20° C. for later analysis.

5. Protein Concentration and Proteolytic Activity

Both protein concentration and proteolytic activity were determined by the methods described in Example 1.

6. pH and Temperature Stability pH stability was determined by preincubating enzyme solution in different buffers at 37° C. for 60 min before the assay of proteolytic activity. Temperature stability was determined by preincubating enzyme solutions at different temperatures for different periods of time before the proteolytic activity assay.

7. Heavy Metal Effect

The effect of heavy metals on proteolytic activity was determined by preincubating a mixture of 5 mM heavy metal stock solution (0.3 ml), 0.2M citrate-phosphate buffer at pH 2.8 (1.6 ml) and enzyme solution (0.1 ml) at room temperature for 10 min before the addition of substrate. All stock solutions of metals were made from chloride salts, except that silver was prepared from the nitrate salt.

8. Inhibitor Effect

The effect of inhibitors on proteolytic activity was determined by preincubating a mixture of inhibitor stock solution (0.05 ml), 0.2M citrate-phosphate buffer at pH 2.8 (1.7 ml) and enzyme solution (0.25 ml) for 10 min at room temperature before the addition of substrate. All inhibitors were from Sigma Co. (St. Louis, MO). The stock solutions were prepared by dissolving the inhibitors either in water or dimethyl sulfoxide (DMSO) as following:

Water—Leupeptin hemisulfate (60 ug/ml), Antipain (60 ug/ml), Poly-L-lysine (60 mg/ml), soybean trypsin inhibitor (60 mg/ml), ovomucoid trypsin inhibitor (60 mg/mL), Tosyl-lysine chloromethyl ketone (TLCK, 60 mM) and iodoacetamide (60 mM).

DMSO—Pepstatin (60 ug/ml), Tosyl-phenylalanine chloromethyl ketone (TPCK, 60 mM), Phenylmethanesulphonylfluoride (PMSF, 60 mM), and Diazoacetylnorleucine methyl ester (DNME, 60 mM).

9. Substrate Specificity

In addition to casein and hemoglobin, bovine serum albumin, fibrinogen, fibrin, elastin and bovine tendon collagen were used to test the general proteolytic activity of the enzymes. The activity against synthetic substrate, α-Benzoyl-DL-arginine p-nitroanilide (BAPNA, BANA), was measured by a method used for papain (Arnon, 1970, *Methods in Enzymology*, 19: 226) with modifications. Forty milligrams of BAPNA was dissolved in 2 ml of DMSO and diluted to 40 ml with water to make a 1 mg/ml substrate solution. A mixture of enzyme solution (0.1 ml), 0.2M citratephosphate buffer (1.9 ml) and BAPNA substrate solution (2 ml) was incubated at 37° C. for 60 min. The reaction was stopped by the addition of 1 ml 33% acetic acid and the amount of p-nitroanilide released was measured at $A_{410}$ against blank.

10. Properties of Three P2.2 Components

The properties of three P2.2 components purified by gel filtration were investigated. PI and PII were found to be similar in many aspects, including temperature and pH profiles, heavy metal and inhibitor effects, and substrate specificity. Molecular weight was the only difference found between PI and PII. It was suspected that PII is a subunit of PI or PI is a proenzyme of PII. Further work would be needed to affirm or reject these hypotheses. In the following discussion a symbol, PI&PII, is adopted to describe either PI or PII owing to their similarity.

a. pH Optima and Stability

Optimum activity of PI&II towards casein and hemoglobin occurs at pH 2.2 and 2.5-2.8, respectively. A small peak towards casein at pH 5.5 is likely an artifact resulted from the insolubility of casein near its isoelectric point. PI&II have very limited activity at pH above 6. The optimum activity of PIII towards hemoglobin occurs at pH 2.8. However, two activity peaks, one at pH 2.8 and another at pH 5.5-5.8, occur when casein is the substrate. Again, low activity towards casein was observed near its isoelectric point. PIII is more active than PI&II at higher pH. The implication of this observation is that the activity peak at pH 5.5 found in the crude extract was mainly contributed by PIII. The purified components were preincubated at different pH for 60 min to test their pH stability. PI&II are stable from pH 2.5-5.0 and PIII is stable from pH 3.0-6.0.

b. Temperature Optima and Stability

PI&II have optimum activity at temperature from 44° to 48° C. PIII exhibits optimum activity at 44° to 46° C. Despite the similar temperature optima, PIII appears more active than PI&II in both temperature extremes. The thermostability of these proteinases was investigated by preincubating the enzymes at most stable pHs, namely pH 3.0 for PI&II and 4.0 for PIII, for different time periods at 37° or 57° C. FIG. 5 reveals that PIII is more heat stable than PI&II. The heat stability of PIII might be attributed to the presence of EDTA and/or cysteine in the enzyme solution, because PIII was found to be a thiol proteinase (infra).

c. Heavy Metal Effect

The effect of various metal ions on the activity of three components is shown in Table 8. PI&II are not sensitive to heavy metals. This observation implies that PI&II are likely to be a carboxyl proteinase, because metal ions were found to produce little inhibition on carboxyl proteinases beyond that attributable to ionic strength (Woessner and Shamberger, 1971, *J. Biolog. Chem.*, 246: 1951). In contrast, PIII is very sensitive to cupric ion and extremely sensitive to mercuric ion, a common property of thiol proteinases. Neither PI&II nor PIII is similar to the copper-activated proteinases found from *Mytilus galloprovincilias* (Iordachescu et al., 1978, *Comp. Biochem. and Physiology*, 61B: 119). Lead ions didn't inhibit PIII under the general assay procedure described in materials and methods. However, when the addition order of buffer and inhibitor solution was reversed, only 20.7% of PIII activity was detected for lead ion, but no apparent difference could be detected for other ions. It appeared that the addition of citrate-phosphate buffer in advance prevented the binding of $Pb^{++}$ to PIII, which was likely due to the binding of $Pb^{++}$ with citrate or phosphate. Despite $Sn^{++}$ has been reported to activate thiol proteinases, such as papain and Aspergillus protease (El-Zalaki et al., 1974, supra). It inhibits PIII slightly.

TABLE 8

| | The effect of metal ions on PI & II and PIII | | | |
|---|---|---|---|---|
| | PI & II | | PIII | |
| Metal ions (0.5 mM) | Activity (HU/ml) | % Retention | Activity (HU/ml) | % Retention |
| Control | 214.7 | 100.0 | 258.7 | 100.0 |
| Ca++ | 209.4 | 97.5 | 256.7 | 99.2 |
| Mg++ | 211.4 | 98.5 | 254.0 | 98.2 |
| Sn++ | 190.6 | 88.8 | 216.5 | 83.7 |
| Pb++* | 214.0 | 99.7 | 250.7 | 96.9 |
| Zn++ | 194.0 | 90.4 | 266.7 | 103.1 |
| Cd++ | 206.7 | 96.3 | 249.4 | 96.4 |
| Hg++ | 187.0 | 87.1 | 0.0 | 0.0 |
| Cu++ | 205.4 | 95.7 | 46.7 | 18.0 |
| Ag+ | 219.3 | 102.2 | 245.8 | 95.0 |
| Ni++ | 206.0 | 96.0 | 239.4 | 92.5 |
| Co++ | 208.0 | 96.9 | 234.7 | 90.7 |

*Abnormal behavior observed (see text).

Almost total inactivation of PIII can be achieved at 1 mM level of cupric ion concentration. PI&II are not sensitive to cupric ions at or below this concentration.

d. Inhibitor Effect

The effect of proteinase inhibitors is shown in Table 9. PI&II are strongly inhibited by pepstatin—a pentapeptide with tow unusual amino acids produced by Streptomyces (Umezawa and Aoyagi, 1971, in *Proteinases in Mammalain Cells and Tissues*, Barrett, ed., North - Holland Pub. Co., Amsterdam, p. 637). Pepstatin is probably a powerful inhibitor of all carboxyl proteinases, with little or no effect on other classes of proteinases. This observation suggests that PI&II are carboxyl proteinases. Further evidence is provided by the fact that PI&II are insensitive to all other inhibitors which commonly inhibit serine and thiol proteinases.

TABLE 9

| The effect of proteinase inhibitors on PI & II and PIII | | | |
|---|---|---|---|
| | | % Residual activity | |
| Inhibitors | Final Conc. | PI & II | PIII |
| Pepstatin | 1 ug/ml | 25.0 | 99.4 |
| Poly-L-lysine | 1 ug/ml | 99.3 | 101.1 |
| PMSF[a] | 1 mM | 102.2 | 53.5 |
| Iodoacetamide | 1 mM | 98.9 | 78.3 |
| TPCK[b] | 1 mM | 96.4 | 21.2 |
| TLCK[c] | 1 mM | 96.2 | 16.8 |
| Soya trypsin inhibitor | 1 mg/ml | 100.5 | 87.4 |
| Ovomucoid trypsin inhibitor | 1 mg/ml | 98.0 | 97.4 |
| Leupeptin hemisulfate | 1 ug/ml | 96.5 | 33.4 |
| Antipain di-HCl | 1 ug/ml | 102.9 | 89.7 |
| DNME | 1 mM | 100.0 | 64.9 |

[a] phenylmethanesulphonylfluoride
[b] tosyl-phenylalanine chloromethyl ketone
[c] tosyl-lysine chloromethyl ketone
[d] diazoacetylnorleucine methyl ester The claim of achieving a pure PI&II are also substantiated by the fact that PI&II were only inhibited by pepstatin, otherwise, PI&II would likely have been inactivated by other inhibitors, especially if the preparation had been contaminated by other groups of enzyme. Carboxyl proteinases, such as cathepsin D and pepsin, are also inhibited by DNME in the presence of the cupric ion. However, PI&II were not sensitive to DNME in the presence of cupric ions even up to 4 hours of preincubation. On the other hand, PIII was very sensitive to DNME even without the presence of cupric ion. PIII was also inhibited by PMSF, Iodoacetamide, TPCK, TLCK and leupeptin. These observations suggests that PIII is a thiol proteinase, because thiol groups are highly reactive. Despite the fact that most of these inhibitors also react with serine proteinases, PIII is ruled out as being a serine proteinase, since it was not inhibited by trypsin inhibitors and needed a thiol compound, such as cysteine, for maximum activity.

e. Substrate Specificity

Depending on the nature of the substrates, proteinases from either same or different groups preferentially attack substrates. For example, alkaline proteinases isolated from sardine stomach hydrolyzed casein more rapidly than hemoglobin. On the other hand, acid proteinases isolated from same source hydrolyzed hemoglobin more rapidly than casein (Noda et al., 1982, *Agric. and Biolog. Chem.*, 46: 1565). Cathepsin D can be rather easily differentiated from pepsin by the fact that serum albumin is hydrolyzed at 10% or less of the rate for hemoglobin (Todd and Trinkojus, 1960, *Biochem. et Biophysica Acta*, 45: 234: Barrett, 1967, *Biochem. J.*, 104: 601) whereas pepsin is equally active against both proteins (Barrett, 1967, supra). The difference is also seen in the resistance of collagen and gelatin to cathepsin D, although they are digested by pepsin (Burleigh, 1977, in *Proteinases in Mammalian Cells and Tissues*, supra p. 285). To help elucidate the identity of the enzymes isolated from clam bellies, the activity of three P2.2 components towards several protein substrates and synthetic substrate, α-Benzoyl-DL-arginine p-nitroanilide (BAPNA), was investigated. As shown in Table 10 both PI&II and PIII are most active against hemoglobin than casein, bovine serum albumin or fibrinogen. Insoluble substrates, such as collagen, elastin and fibrin, are not degraded by either PI&II or PIII.

TABLE 10

Relative activity of PI & II and PIII towards different substrates

| Substrate | Relative activity (%) PI & II | PIII |
|---|---|---|
| Hemoglobin | 100.0 | 100.0 |
| Casein | 30.3 | 23.8 |

TABLE 10-continued

Relative activity of PI & II and PIII towards different substrates

| Substrate | Relative activity (%) PI & II | PIII |
|---|---|---|
| Bovine serum albumin | 26.0 | 34.7 |
| Fibrinogen | 34.2 | 27.2 |

PIII can attack BAPNA—a synthetic substrate for papain, bromelain, trypsin and cathepsin B. Optimum pH for this substrate shifts to 6.0–6.5. The observation is similar to that of cathepsin B, which has a lower pH optimum towards protein substrate (Burleigh et al., 1974, *Biochem J.*, 137: 387; Otto, 1971 *Tissue Proteinases*, Barrett et al., ed., North-Holland Pub. Co., Amsterdam, p. 1), but higher pH optimum towards synthetic substrates (Barrett and Kirschke, 1981, supra,). PI&II have no activity towards BAPNA.

f. Comparison with Cathepsin D and B

PI&II are carboxyl proteinases. Among most important carboxyl proteinases discovered in mammalian viscera tissues are pepsin, gastricin, chymosin, renin and cathepsin D. A comparison of PI&II with these enzymes suggests that PI&II are cathepsin D-line enzymes. PI&II are ruled out as being pepsin-like or gastricin-like enzymes due to their insensitivity to poly-L-lysine (Reid and Rauchert, 1970, supra) and the preference of hemoglobin as substrate. Similarly, a comparison of PIII with thiol proteinases, such as cathepsin B, H and L, indicates that PIII is a cathepsin B-like enzyme. PIII differs from cathepsin L, since the latter can not attack BAPNA (Barrett, 1977a, supra). PIII differs from cathepsin H, since the latter is rather insensitive to leupeptin (Barrett and Kirschke, 1981, supra). The properties of PI&II, PIII, mammalian cathespin D and B are summarized in Table 11. Despite much resemblance, PI&II and PIII are smaller than their mammalian counter-parts. The molecular weights in parentheses are those of high molecular weight forms found in clam or mammal. PI&II also differ from cathespin D in the sensitivity to DNME in the presence of cupric ion. PIII has a lower pH optimum towards casein and hemoglobin than mammalian cathespin B.

TABLE 11

Summarized properties of PI & II and PIII as compared with mammalian cathepsin D[a] and B[b]

| Properties | PI & II | Cathepsin D | PIII | Cathepsin B |
|---|---|---|---|---|
| Molecular weight | 36,700 (77,200) | 42,000 (100,000) | 17,400 | 24,000 |
| pH optima | | | | |
| casein | 2.2 | ? | 2.8, 5.5 | 6.0 |
| hemoglobin | 2.8 | 2.8–3.5 | 2.8 | 4.0–4.5 |
| pH stability | 2.5–5.0 | unstable at pH > 7 | 3.0–6.0 | unstable at pH > 7 |
| Temperature optima | 44–48° C. | 45° C. | 42–46° C. | 40° C. |
| Temperature stability | | | | |
| 37° C., 90 min | 86.7% (pH 3) | ? | 100% (pH 4) | ? |
| 57° C., 90 min | 3.8% (pH 3) | ? | 71.4% (pH 4) | ? |
| Inhibitors | | | | |
| Heavy Metal | | | | |
| Cu++ | − | − | + | + |
| Hg++ | − | − | + | + |
| Pepstatin | + | + | − | − |
| Leupeptin | − | − | + | + |
| DNME w/Cu++ | − | + | + | + |
| TLCK | − | − | + | + |
| TPCK | − | − | + | + |
| Activators | none | none | EDTA Cys-C + HCl | EDTA Cys-HCl |

TABLE 11-continued

Summarized properties of PI & II and PIII as compared with mammalian cathepsin D[a] and B[b]

| Properties | PI & II | Cathepsin D | PIII | Cathepsin B |
|---|---|---|---|---|
| Attack BAPNA[c] | — | — | + | + |

[a]sources: Barrett, 1977c; Takahashi and Tang, 1981.
[b]sources: Barrett, 1977b; Barrett and Kirschke, 1981.
[c]α-Benzoyl-DL-arginine p-nitroanilide

11. Miscellaneous Observations a. Accumulative Effect of PI&II and PIII

Since the pH optima of these enzymes are so similar, the total activity measured in the presence of both PI&II and PIII, such as in crude extract, might be the synergistic effect of these enzymes or the opposite. As shown in Table 12 the activity level of different combinations of purified PI&II and PIII is the same as the calculated sum of individual enzyme activity. The effect of these enzymes appeared to be accumulative. However, a synergistic effect was reported for cathepsin B and D (Huang et al., 1979, *J. Biolog. Chem.*, 254: 11405).

TABLE 12

The accumulative effect of PI & II and PIII

| Enzyme mixture | | Observed activity | Calc. sum activity |
|---|---|---|---|
| PI & II (ml) | PIII (ml) | (HU/ml) | (HU/ml) |
| 0.100 | 0.000 | 232.0 | — |
| 0.075 | 0.025 | 239.3 | 240.5 |
| 0.050 | 0.050 | 253.3 | 249.0 |
| 0.025 | 0.075 | 256.7 | 257.5 |
| 0.000 | 0.100 | 266.0 | — | b. Purity and Yield Factors of Each Fractionation Step

The relative activity ratio of PI&II and PIII in each purification step could be estimated by the addition of a specific inhibitor of PI&II or PIII. The difference between the activity measured without inhibitor and with inhibitor is contributed by the enzyme sensitive to this inhibitor. The addition of 1 mM of cupric ion appeared to completely inhibit PIII, but had little effect on PI&II. Thus, the purity and yield factors from each purification step were obtained for each enzyme by reanalyzing the samples with and without 1 mM cupric ion in the assay mixture. Overall, PI&II were purified 22.5-fold with a recovery of 36.3% and PIII was purified 98.2-fold with a recovery of 59%.

c. Differential Distribution of PI&II and PIII in Ethanol Fractions

As described in Example 2, 40–70% ethanol fraction was selected on the basis of higher recovery of total activity. Following the discovery of these different enzymes with similar pH optimum, it was necessary to reinvestigate this process to see whether different ethanol fractions can preferentially fractionate these enzymes. This fractionation might have occurred in the previous study, but was not detected due to similar pH optima. As shown in Table 14, the 40–70% ethanol fraction has PI&II/PIII ratio similar to 10-fold ultrafiltration concentrate. However, 40–55% ethanol fraction is more rich in PIII and 55–70% ethanol fraction is more rich in PI&II. This observation suggests that PI&II, like cathepsin D, are glycoproteins which tend to be more stable at higher ethanol concentration (Barrett, 1977c, supra).

TABLE 14

Differential distribution of PI & II and PIII in ethanol fractions

| Ethanol (% v/v) | Activity w/o Cu++ (HU/ml) | Activity w/ Cu++ (HU/ml) | % PI & II | % PIII | PI & PII/PIII ratio |
|---|---|---|---|---|---|
| 10x conc. | 2195.5 | 1311.1 | 63.9 | 36.1 | 1.77 |
| 40–70 | 1641.5 | 1013.3 | 66.0 | 34.0 | 1.94 |
| 40–55 | 734.2 | 200.9 | 29.3 | 70.7 | 0.41 |
| 55–70 | 896.0 | 778.7 | 93.0 | 7.0 | 13.30 |

12. Conclusions

Two distinct proteinases have been characterized and identified. PI&II, being carboxyl proteinases, are similar to mammalian cathepsin D. PIII, being a thiol proteinase, is similar to mammalian cathepsin B. Many carboxyl proteinases of diverse origins, such as microbial acid proteinases, mammalian pepsins and cathepsin Ds, are homologus in their amino acid sequences (Takahashi and Tang, 1981, *Methods in Enzymology*, 80: 565). Similarly, thiol proteinases, such as papain and cathepsin B, have a very similar amino acid sequence around the catalytic site as to leave no reasonable doubt of the evolutionary homology of these enzymes (Takio et al., 1980, *Biochem. and Biophysical Res. Comm.*, 92: 340).

EXAMPLE 3

TABLE 13

Purity and yield factors of PI & II and PIII in each purification step

| | PI & II | | | | PIII | | | |
|---|---|---|---|---|---|---|---|---|
| Fraction | Total protein (mg) | Total activity (CU) | Specific activity (CU/mg) | Yield (%) | Total protein (mg) | Total activity (CU) | Specific activity (CU/mg) | Yield (%) |
| Water extract | 3910 | 44,553 | 11.4 | 100.0 | 3910 | 23,749 | 6.1 | 100.0 |
| Acidified-Stabilized extract | 845 | 43,545 | 51.5 | 97.7 | 845 | 28,789 | 34.1 | 121.2 |
| 25x UF Concentrate | 576 | 41,355 | 71.8 | 92.8 | 576 | 26,322 | 45.7 | 110.8 |
| 40–70% ETOH fraction | 177 | 29,590 | 167.2 | 66.4 | 177 | 21,420 | 121.0 | 90.2 |
| Biogel p-150 column | 63 | 16,190 | 255.8 | 36.3 | 23 | 14,004 | 596.0 | 59.0 |

Evaluation of Cathepsin B-like Enzyme from Clam Viscera as Rennet Substitute for Cheese-making Milk coagulation can be achieved either by the acidification of milk or by the addition of a suitable clotting enzyme. In this Example the term 'milk coagulant' or 'coagulant' exclusively refers to the enzymes which clot milk. The coagulant traditionally used for cheese-making in most of the world is rennet extract from the abomasa of 10 to 30-day-old milk-fed calves. There has been a continued interest in finding rennet substitutes, because a world-wide shortage of rennet has arisen from an increase in cheese-making combined with a decline in the number of calves slaughtered (Green, 1977, *J. Dairy Res.*, 44: 159). For instance, cheese production in the U.S.A. increased from about 0.68 million tonnes in 1960 to 1.2 million tonnes in 1973, with a corresponding decrease in commercial calf slaughter from about 8 million to about 2 million (Cheeseman, 1981, *Enzyme and Food Processing*, Birch et al, eds., Appl. Sci. Pub., London). Even if complete utilization of calf stomach for rennet production had occurred, the potential supply would have been insufficient by 1969. To meet demands, substitute products were developed and currently several rennet substitutes are commercially available. These are fungal rennets from *Endothia parasitica*, *Mucor miehei* and *Mucor pusilus*, 50:50 calf rennet and pepsin mixture, Bovine rennet and chicken pepsin. Commercial use of chicken pepsin as milk coagulant can only be found in Israel.

It was suggested that in 1977 no more than 15% of cheese made in the U.S.A was made with rennet alone. Some 40% was made with rennet-pepsin mixtures and 40% from Mucor rennets. It is likely that the proportion made from calf rennet alone has decreased even further since then.

Despite the existence of these substitutes, traditional calf coagulant is still preferred by most cheese manufacturers, simply because none of these rennet substitutes can totally replace the unique characteristics of calf rennet. The objective of this portion of the overall study was to investigate the possibility of using cathepsin B-like enzyme isolated from clam waste as a rennet substitute for cheese-making. Cathepsin D-like enzyme was ruled out as being a possible substitute due to its instability and very low clotting activity at pH above 6.0.

1. The Role of Milk Coagulant in Cheese-making

The coagulation of milk by enzyme for cheese production consists of a minimum of three distinct phases. The first phase involves the enzymatic hydrolysis of specific bonds, especially phe-met bond, in κ-casein which results in destruction of the protective effect κ-casein has on the casein micelle. The second phase, aggregation, is a result of association of the destabilized micelles. The third phase, general proteolysis, progresses simultaneously with primary and secondary phases, and during the ripening of the cheese. The specific requirements of each phase make a suitable coagulant hard to find.

2. The Requirements for a Suitable Milk Coagulant

The points of major interests to the cheese-maker regarding coagulants include cheese yield, cheese quality and the strength and price of the coagulant (Tofte Jespersen and Dinesen, 1979, *J. Soc. Dairy Tech.*, 32: 194). Those factors are, in turn, determined by the following properties of the coagulant preparations:

a. Clotting Versus Proteolytic Activity

The ratio of milk clotting activity to proteolytic activity is often used to assess the suitability of enzymes as rennet substitutes (Green, 1972, *J. Dairy Res.*, 39: 261). It is generally believed that only those enzymes which have limited proteolysis in the casein coagulum are suitable for the production of cheeses. Calf rennet is ideal for cheese production because of its limited and specific clotting activity to general proteolytic activity. Most substitutes are more proteolytic than calf rennet relative to their clotting activity (Martens and Naudts, 1973, *An. Bull. Int. Dairy Fed.*, 24: 1). If the proteolytic activity is excessive, the yield of cheese and retention of fat by the curd may diminish. Excessive proteolysis during ripening also has undesirable effects of the body and flavor of the finished cheese (Martens and Naudts, 1973, supra). On the other hand, lack of proteolytic activity during ripening also results in textural defects and slow flavor development (Melachouris and Tuckey, 1964, *J. Dairy Sci.*, 47: 1; Maragoudakis et al., 1961, *J. Dairy Sci.*, 44: 239).

b. Proteolytic Specificity

As well as forming the milk gel, milk coagulant also plays a part in the ripening of cheese. Different rennets because of the differences in proteolytic specificity, will give rise to a range of breakdown products that differ in composition (Vanderpoorten and Weckx, 1972, *Natl. Milk and Dairy J.*, 26: 47). The hydrolytic changes occurring during ripening are not only important in regard to flavor development, but also influence changes in body and texture of the cheese. One of the major concerns about cheese quality is the development of bitter flavor. The ultimate degree of bitterness is determined by the type and amount of rennet retained in the cheese (Stadhouders, 1978, *20th Int. Dairy Cong. Conf.*, Paris, 392T) as well as by the choice of starter culture (Lawrence et al., *N.Z. J. Dairy Sci. & Tech.*, 7: 32: Lowrie and Lawrence, 1972, *N.Z. J. Dairy Sci & Tech.*, 7: 51).

c. Curd Properties

For satisfactory cheese-making, it is essential that the coagulant and conditions used will produce a curd of desired physical properties. The firmness and syneresis should be similar to those when calf rennet is used and there should be no significant loss of fat or protein at these stages.

d. Coagulant Composition

Most coagulants contain more than one proteinase component responsible for the coagulation of milk besides nonproteolytic enzymes such as lipase and cellulase. The cheese-making and ripening processes may be affected by the variation in the proportions of these enzymes. The greater tendency to produce soapy and rancid off-flavors in cheese made with fungal rennets might be attributed to the incorporation of lipase into the curd (Green and Stackpoole, 1975, *J. Dairy Res.*, 42: 297). The presence of cellulase in the coagulant produced from fungal source is undesirable as it shortens the life of the cotton press clothes (Nelson, 1975, *J. Dairy Sci.*, 58: 1739). It would seem desirable that the content of different proteolytic, lypolytic and cellulolytic components of commercial coagulants be standarized to minimize product variations.

3. Milk Coagulants of Diverse Origins

As almost all organisms probably produce proteinases and many of these enzymes induce clotting of milk, the potential area of search for rennet substitutes is enormous. Numerous investigations have been published on the use of rennet substitutes from plant, animal or microbial sources (Ernstrom, 1974, *Fund. Dairy Chem.*, 2nd ed., Webb et al, eds., AVI Pub. Co., Westport, Conn., 662). However, few investigations have shown real promise. Two particular problems arise in the use of rennet substitutes which have to be overcome for satisfactory cheese-making:

(1) Losses of proteins are often greater during cheese-making with rennet substitutes, and this will lower the yield.

(2) Differing proteolytic specificity may alter the ripening characteristics of the cheese, giving rise to off-flavors.

a. Milk Coagulant from Plant Sources

A number of proteolytic enzymes from plants, such as papain, ficin and bromelain, will clot milk but most plant coagulants have proved too proteolytic for use in cheese-making. The most common criticism of these cheese products is that they produce flavor defects caused by bitter peptides (Davis, 1971, *Dairy Industries*, 36: 135).

b. Milk Coagulants from Animal Sources

The gastric proteases, specifically pepsin, in the stomachs of animals are potential rennet substitutes, because they are expected to have properties in common with chymosin, which is the major constituent of calf rennet responsible for the coagulation of milk. Porcine pepsin might be sued as a rennet substitute provided that the cheese can be ripened for longer periods than is necessary with calf rennet (Melachouris and Tuckey, 1964, supra). However, its ability to clot milk diminish rapidly above pH 6.5. Bovine pepsin will clot milk up to pH 6.9, and is about equal in clotting to proteolytic ratio with rennet (Green, 1972, *J. Dairy Res.*, 39: 261),but the enzyme gives rise to differences in texture and flavor (Stanley and Emmons, 1977). Although chicken pepsin has higher pH optima and stability than swine pepsin (Bohak, 1970, *Methods in Enzymol.*, 19: 347), the cheese made from chicken proventriculae extract had intense off-flavors in addition to poor body (Green, 1972, supra). Cheddar Cheese made from the gastric extract of harp seal cubs was claimed to have higher quality score than the cheese made from calf rennet (Shamsuzzaman and Haard, 1983, *J. Food Sci.*, 48: 179), but the supply of stomachs from seal cubs is insufficient and fluctuating.

c. Milk Coagulants From Microbial Sources

The great economic advantage of using microorganisms for the production of enzymes has stimulated a lot of research in screening and developing microbial rennets.

(1) Fungal Rennets

The most important commercial microbial rennet preparations now on the market come from the fungal species *Endothia parasitica, Mucor miehei* and *Mucor pusillus*. Favorable results have been reported from the use of these fungal rennets (Ernstrom, 1974, supra). However, some minor criticism have been made, again largely concerning bitterness (Richardson et al., 1967, *J. Dairy Sci.*, 50: 1066). Babel, (1967, *Dairy Industries*, 32: 901) found that cheddar cheese made from *Mucor pusillus* rennet had a coarse grainy texture, and rancid flavor develops in a short time if the preparation is not freed from lipase. A further point of possible importance was the observation that a substance inhibitory to lactic cultures may be present (Babel and Somkuti, 1968, *J. Dairy Sci.*, 51: 937). Emmons and Beckett, (1977, *J. Dairy Sci.*, 60(sup 2): 47) showed that the fungal coagulants had a distinctly higher loss of proteins to whey than calf rennet. An acid protease from a species of *Rhizopus* was found to be too proteolytic for satisfactory cheese-making (Phelan, 1973, *Dairy Industries*, 38: 418).

(2) Bacterial Rennets

Of the bacterial proteinases, those from the genus *Bacillus* have received most attention. *Bacillus subtilis* produces extracelluar alkaline, neutral and acid proteinases. All have a much lower ratio of milk clotting to proteolytic activity than does calf rennet (Puhan and Irvine, 1973, *J. Dairy Sci.*, 56: 323), and catalyze extensive hydrolysis of $\beta$-casein (Puhan, 1969, *J. Dairy Sci.*, 52: 1372). *Bacillus polymyxa* proteinase is too proteolytic to be suitable for the manufacture of several cheese varieties (Phelan, 1973, supra). *Bacillus mesentericus* proteinase showed promising for the manufacture of some semi-hard cheese varieties. However, proper pH control during cheese-making is necessary to prevent an over proteolytic action by this enzyme (Mesrob and Stoeva, 1978, *Milchwissenehaft*, 33: 483).

(3) Yeast Rennets

The study of proteolytic activity among yeast is much less intense than the work done on the fungal and bacterial proteinases. The ability to liquefy gelatin and to clot milk by yeasts has been recognized long ago (Sacchetti, 1933, *Archiv. Mikrobiolog.*, 4: 427). More recently, the distribution of extracellular proteases in yeasts have been reviewed (Ahearn et al., 1968, *Appl. Microbiol.*, 16: 1370; Kamada et al., 1972, *Nippon Nogei. Kaishi*, 46: 171). However, during the screening of 143 yeasts for proteolytic and milk clotting activity (Alessandro and Federico, 1980, *J. Dairy Sci.*, 63: 1397) found that only one strain produced extracellular protease in shake culture and the yield was low. This yeast proteinase is heat-stable. In this instance, it resembles the clotting enzymes from fungal rennets (Duersch and Ernstrom, 1974, *J. Dairy Sci.*, 57: 590). The heat stable clotting enzymes are undesirable because with increasing use of whey as ingredients in formulated foods, it is not likely to inactivate these proteinases by a heat treatment without altering whey proteins (Hyslop et al, 1979, *J. Dairy Sci.*, 62: 1227).

4. Changes in the Manufacturing Process

Raising the coagulation temperature, addition of calcium chloride to milk and acidification of the milk before renneting all reduce the amount of the coagulant required to clot the milk in a given time period. Calcium chloride affects the coagulability of the milk. On the other hand, pH and temperature affect the activity of the enzyme (Ernstrom, 1974, supra).

b. Use of Concentrated Milk

Only 20–25% of the normal amount of rennet was required to coagulate the milk concentrated 2x by ultrafiltration (Chapman et al., 1974, *J. Soc. Dairy Tech.*, 27: 151).

c. Use of Immobilized Coagulant

The most economic way of conserving coagulant is to use a reactor containing immobilized coagulant for the continuous catalysis of milk clotting reaction. However, such a system is difficult to use when the end-product is a coagulum which would clog the reactor. Fortunately, the enzymatic and aggregation stages of clotting can be separated because the later stage has a high temperature coefficient (Berridge, 1942, *Nature*, 149: 193). The primary enzymatic stage can be carried out below 15° C. (at the expense of lower reaction rate), after which raising the temperature of the milk to 25°-30° C. induces aggregation. Pepsin immobilized by covalent binding to porous glass has been reported to catalyze the enzymatic stage of milk clotting (Ferrier et al., 1972, *J. Dairy Sci.*, 55: 726). Later work indicated that a fluidized bed reactor gave improved performance over a packed column (Cheryan et al., 1975, *Biotech. & Bioengin.*, 17: 585). Chymosin (Beeby, 1979, *N.Z.J. Dairy Sci. & Tech.*, 14:1: Brown and Swaisgood, 1975, *J. Dairy Sci.*, 58: 796) and fungal proteases from *Mucor miehei* and *Endothia parasitica* (Beeby, 1979, supra) have also been immobilized on various supports.

All these immobilized enzyme preparations are subjected to loss of activity, particularly during use. There is also a tendency to alter the enzyme specificity that the attack upon the phe(105)-met(106) bond of κ-casein diminishes and more general proteolysis becomes the dominant reaction (Beeby, 1979, surpa). Considerable progress remains to be made before a successful continuous coagulation system can be used commercially. Cheryan (1976, *Biotech. & Bioengin.*, 18: 273) and co-workers suggested that more research is needed particularly in finding more suitable carriers.

The development of ultrafiltration and immobilized coagulant may reduce the amount of rennet needed to drastically that the use of rennet substitute for milk coagulation becomes obsolete. However, it is important to know that the quality of cheese made by reduced amount of rennet will be inferior to that of regular cheese, because the amount of rennet incorporated into the coagulum plays an important role in the ripening of cheese. One of the possible solutions to this problem is to incorporate another proteinase to accelerate the ripening of cheese. Another approach is to mix with a source of intense cheese flavor, either synthetic or fermented, as it is being practiced in imitation cheese products. Nevertheless, cheeses produced by traditional process is still likely to dominate the market for a long time before any drastical changes.

5. Milk Coagulant Preparation a. Calf Rennet

Commercial single strength calf rennet (Pfizer Inc., New York, N.Y.) diluted 1:20 with water was used for milk clotting time determination. Same stock rennet solution diluted 1:40 was used for cheese-making. All dilutions were made 5 min before use.

b. Porcine Pepsin

A 0.2 mg/ml solution of two-time crystallized and lyophilized powder of porcine pepsin (Sigma Co., St. Louis, Mo.) was used to measure milk clotting time. The solution was prepared daily in 0.005 M citrate-phosphate buffer pH 4.2. The specifications of the pepsin lot were 2900 units/mg solid and one unit will produce an increase in $A_{280}$ of 0.001 per minute at pH 2.0 and 37° C., using hemoglobin as substrate and a reaction volume of 16 ml.

c. Clam Rennet

Crude extract from clam viscera prepared according to the method described in Example 1 was acidified to pH 3.2. After the removal of precipitated proteins by centrifugation, the pH of the supernatant was adjusted to 4.2 with 2 N NaOH. Five hundred milliliters of this supernatant was then concentrated 10 times by ultrafiltration using the similar ultrafiltration conditions described in Example 1, except that the membrane was replaced by PM-30 membranes with a 30,000 molecular weight cut-off. Forty millimeters of the retentate was then fractionated with ethanol. The 40-55% ethanol fraction, which is rich in cathepsin B-line enzyme (Table 14), was dissolved in 8 ml of 10 mM cysteine-HCl solution with pH adjusted to 4.2 by 0.5 N NaOH. This newly prepared clam rennet was allowed to stand at room temperature for 30 min before use in order to fully activate the cathepsin B-line enzyme. FIG. 6 shows the time course of activation of clam rennet as determined by milk clotting time.

6. Milk Clotting Time Determination

The clotting activity of milk coagulants was determined according to the method of Berridge, with modifications (1952, *The Analyst*, 77: 57). To 0.05 ml (unless otherwise mentioned) of milk coagulant placed in a 25-ml test tube was added 10 ml of tempered substrate solution. The substrate solution was 10% reconstituted skim milk powder containing 10 mM $CaCl_2$. The pH of this substrate solution was approximately 6.2. Where indicated, the pH of the substrate solution was adjusted with 0.5 N NaOH or HCl while agitating. The mixture of coagulant and substrate was then incubated at 30° C. water bath unless specifically indicated. Near the expected clotting time, which was determined by a preliminary test, the test tube was tilted ~60° at an interval of 5 seconds. The moment of the first flake appearance of the liquid flowing down the tube was recorded as milk clotting time.

7. Proteolytic Activity Determination

Milk coagulants were assayed for proteolytic activity according to the method described in Example 1.

8. Cheddar Cheese Manufacture

Raw milk obtained from a milk supply produced by the Cornell Dairy Herd was pasteurized at 72° C. for 15 sec. Cheese starter culture, containing *Streptococcus lactis* and *Streptococcus cremoris*, was obtained from frozen concentrate (Marschall Products, Miles Laboratories, Inc., WI). The starter culture was transferred and propagated three times in skim milk heated to 90° C. for 60 min. Two portions of the pasteurized milk, each 13.636 Kg, were made into cheddar cheese according to the method of Dzurec, (1982, Ph.D. Thesis, Cornell U., 94) adapted from the method of Kosikowski, (1977, Cheese & Ferm. Milk Foods, 2nd ed., Edward Bros., Ann Arbor, Mich.). Both clam rennet and calf rennet were used to make cheddar cheese. Same procedures were followed, except that the renneting-to-cut time of clam rennet was prolonged to 50 min instead of 25 min commonly practiced by calf rennet. The ratios of rennet to milk were equivalent to the ratios used in curd firmness determination. Small wheels of finished cheeses were waxed and allowed to ripen in a 10° C. curing room. Cheese samples were periodically taken from finished products and subjected to select types of analysis.

9. Cheese Yield and Composition Determination

Cheese was determined gravimetrically before waxing. The moisture contents of milk, cheese and whey were determined according to the atmospheric oven method (Bianco et al., 1978b, *Stand. Meth. Exam. Dairy Products*, 14th ed., Am. Public Health Ser., Washington, D.C. 231). Fat contents were determined by modified Babcock methods (Bianco et al., 1978b, supra, 369). Protein contents was calculated by multiplying the percent Kjeldahl nitrogen by 6.38. Samples were prepared according to Rowland's (1938, *J. Dairy Sci.*, 9: 30 & 42) method for the determination of total Kjeldahl nitrogen and nonprotein Kjeldahl nitrogen. Kjeldahl nitrogen was determined using a Tecator Kjeltec System I apparatus (Tecator Inc., Boulder, Colo.).

10. Determination of Soluble Nitrogen, Tyrosin and Tryptophan in Cheese Extract The amounts of soluble nitrogen, tyrosine and tryptophan in a clear sodium citrate-hydrochloric acid extract of cheese were determined according to the method of Vakaleris and price (1959, *J. Dairy Sci.*, 42: 264) with minor modifications. Five grams of cheese, 20 ml of 0.5 M sodium citrate solution and 43 ml of distilled water were mixed in a Waring blender at high speed for 7 min. The homogeneous milky solution was diluted to 100 ml. Ten milliliters of 1.41 N HCl and 15 ml of water were added to this solution while mixing. The mixture was then filtered through Whatman 42 filter paper. A clear sodium citratehydrochloric acid extract was thus obtained and referred as cheese extract. The amount of soluble nitrogen in cheese extract was measured spectrophotometrically at $A_{274.5}$ using the cheese extract diluted with same volume of distilled water. The amounts of tyrosine and tryptophan in the cheese extract were determined by applying the following equations:

$$M_{tyr} = (0.95 \, E_{270} - 1.31 \, E_{290}) \times 10^{-3}$$

$$M_{trp} = (0.307 \, E_{290} - 0.020 \, E_{270}) \times 10^{-3}$$

where $M_{tyr}$ and $M_{trp}$ express moles/l of tyrosine and tryptophan, respectively and where $E_{270}$ and $E_{290}$ are the optical density values of the cheese extract at 270 and 290 nm, respectively. Solvent which was made with 20 ml of 0.5M sodium citrate solution, 10 ml of 1.41 N HCl and 220 ml distilled water was used as blank.

11. Alkaline Urea-polyacrylamide Gel Electrophoresis of Cheese Samples

Cheese samples were taken from both clam and calf cheese and kept frozen at −20° C. every two weeks. After 8 weeks, 0.2 gram of cheese from each sample was mixed with 2 ml of modified Poulick's buffer containing 35 ml of stock Poulick's buffer (Poulick, 1957, *Nature*, 180: 1477), 205 ml distilled water and 147 g urea. The mixture was boiled for 15 min to dissolve cheese proteins. To 1 ml of cheese solution were added one drop of dye marker, one drop of 2-mercaptoethanol and 0.3 ml of 40% sucrose solution. The electrophoresis was then carried out according to the alkaline urea-polyacrylamide method as described by Kiddy, (1975, *Meth. Gel. Electrophoresis of Milk Proteins*, Swaisgood et., Am. Dairy Sci. Assoc., 14).

Thoroughly destained gel was scanned in an E-C densitometer (E-C Corporation, St. Petersburg, Fla.) interfaced with Apple II plus computer (Apple Computer Inc., Cupertino, Calif.), which was loaded with LAB DATA MANAGER 1 (LDB1) software (Interactive Microware, Inc., State College, Pa.), to plot the relative peak heights of the protein bands.

12. Sensory Evaluation of Cheese

Ten-week-old cheeses were evaluated by preference tests. Ten panelists randomly selected from graduate students in the Department of Food Science at Cornell University were provided four different symbol-coded cheese samples. Two samples were from clam cheese and the other two from calf cheese. Samples were randomized among panelists. Each panelist was asked to rate the flavor, texture and body, and overall acceptability of the samples on a 9-point hedonic scale (9-like extremely; 5-neither like or dislike; 1-dislike extremely).

13. Characterization of Milk Coagulants

The ratio of milk clotting activity to proteolytic activity against hemoglobin is often used to assess the suitability of enzymes as rennet substitute (Green, 1972, supra). The relative ratios for clam rennet, porcine pepsin and calf rennet are summarized in Table 15. Clam rennet had considerably lower ratio of clotting to hemolytic activity at optimum pH of each individual enzyme. The ratio of clotting to caseinolytic activity at milk clotting pH was also examined, since this condition approximated more closely to what really happened during cheese-making. Clam rennets appeared to have even lower ratio of clotting to proteolytic activity under this condition. These observations indicates that clam rennet is more active in protein hydrolysis in equivalent clotting units of porcine pepsin or calf rennet. The effects of the high proteolytic activity of clam rennet will be discussed in later sections.

TABLE 15

| | The relative ration of clotting to proteolytic activity of different rennets at 30° C. | |
|---|---|---|
| | Substrate | |
| Milk coagulant | Hemoglobin | Casein |
| Calf rennet | 1.00 (3.7[a]) | 1.00 (6.2[d]) |
| Porcine pepsin | 0.30 (1.8[b]) | 0.24 (6.2) |
| Clam rennet | 0.13 (2.8[c]) | 0.03 (6.2) |

[a]optimum pH of chymosin (Foltmann, 1970).
[b]optimum pH of porcine pepsin (Ryle, 1970).
[c]optimum pH of cathepsin B-line clam proteinase (see chapter 2).
[d]pH of milk clotting assay b. Coagulant Concentration Effect on Milk Coagulation

The relative clotting activity of milk coagulants can be approximated by the milk clotting time. All three coagulant preparations had equivalent clotting activity when 0.05 ml of each coagulant was used. However, the clotting power of clam rennet was higher than the other two coagulants when larger amounts of coagulant were used. On the other hand, the clotting power of clam rennet decreased more rapidly as smaller amounts of coagulant were used and calm rennet failed to clot the milk at 0.02 ml level. The gastric protease from harp seal (Shamsuzzaman and Haard, 1982, supra) and chicken pepsin (Gordin and Rosenthal, 1978, *J. Food Protect.*, 41: 684) were also reported to lose activity at low enzyme concentration. This observation suggests that the reaction kinectics (mechanism) of clam rennet might differ from those of porcine pepsin and calf rennet, since clam rennet (Cathepsin B-like) contains mainly a thiol proteinase which differs from carboxyl proteinases, such as pepsin and chymosin, in catalytic mechanism. Another possibility is that natural inhibitors to clam rennet exist in milk. The latter inference is supported by the fact that a heat-labile thiol proteinase inhibitor has been isolated from raw milk (Reimerdes et al., 1976, *Milchwissenchaft*, 31: 329) after the discovery of more profound proteolysis by plant proteases, such as papain, ficin and bromelain, in heat-treated milk than non-heat-treated milk (Klostermeyer et al., 1975, *Milchwissenchaft*, 30: 194).

Since the reaction rate of an enzyme-catalyzed reaction is proportional to enzyme concentration, the product of enzyme concentration and time is constant for any given amount of reaction (Ernstrom, 1974, supra). By the criterion of the visible appearance of clots in renneted milk, it is possible to define very simply the rate of the clotting reaction, which is the reciprocal of milk clotting time. To a first approximation, it has long been established that the clotting time is inversely proportional to the concentration of clotting enzyme (Storch and Segelcke, 1874, *Milchzeiyung*, 3: 977):

$$(1/t_c) = \kappa C \quad \text{(eq. 3-1)}$$

where $t_c$ is the milk clotting time, $\kappa$ is the rate constant and C is the concentration of the enzyme. This approximation forms the basis for the assay of clotting activity of many enzymes (Kopelman and Cogan, 1976, *J. Dairy Sci.*, 59: 196). However, the appearance of visible clots is the result of two partially overlapped reactions, the enzymatic attack on κ-casein and the aggregation of casein micelles. It has been shown that more than 80% of κ-casein must have been split before micelles showing aggregation tendency (Dalgleish, 1982, *Dev. in Dairy Sci.*, 1: 157) and at least 90% of the total κ-casein in milk has been hydrolyzed at the visually observed clotting time (Chaplin and Green, *J. Dairy Res.*, 47: 351). Based on the assumption that the enzymatic and aggregation phases are sequential, a two-term equation was postulated (Foltmann, 1959, *15th Int. Dairy Cong.*, London, 2: 655):

$$t_c = t_o + (K/C) \quad \text{(eq. 3-2)}$$

where $t_c$ is the clotting time, $t_o$ is the time required for aggregation or time delay of the system and K/C represents the time for the enzymatic stage, K and C being a constant and the concentration of enzyme, respectively. Equation 3-2 was demonstrated to be a better estimation than equation 3-1 at low coagulant concentration. A third equation, which adds another term to equation 3-1, has also been used recently (Cogan et al, 1982, *J. Dairy Sci.*, 65: 1130):

$$(1/t_c) = (1/t_o) + \kappa C \quad \text{(eq. 3-3)}$$

where all symbols have been defined as in equation 3-2 or 3-3. Equation 3-3 has been shown to be linear for chicken pepsin in the temperature range from 27.5° to 62.5° C.

Both porcine pepsin and calf rennet followed equation 3-2 closely as indicated by the high linear correlation coefficients ($R^2$) in Table 15. The y-intercepts, which are $t_o$s, appeared to be negligible for both calf rennet and porcine pepsin, i.e. the equation 3-2 degenerated to equation 3-1 in the range of enzyme concentration examined. However, the relationship between $t_c$ and 1/C of clam rennet appeared to be nonlinear. The forced regression line would yield an y-intercept that is negative and far away from zero. The negative y-intercept suggests that clam rennet can't be characterized by equation 3-2, since y-intercept represents the time required for micelle aggregation and is unlikely to be negative.

Thus, the data were replotted using equation 3-3. All three coagulants had very high linear correlation coefficient as shown in Table 16. The y-intercepts, which are micelle aggregation rate, appear to be negligible for both porcine pepsin and calf rennet. Again, equation 3-3 degenerates to equation 3-1 for both enzymes.

TABLE 16

| | Linear regression parameters | | | |
| Coagulant | Number of observation | Slope | Intercepts X- | Intercepts Y- | Correlation coefficient ($R^2$) |
| --- | --- | --- | --- | --- | --- |
| Clam rennet | 8 | 53.7 | 10.4 | −560.0 | .8774 |
| Porcine pepsin | 10 | 16.5 | 1.9 | −8.7 | .9995 |
| Calf rennet | 10 | 15.0 | −0.3 | 5.0 | .9999 |

The high linear correlation coefficient suggests that clam rennet can be characterized by equation 3-3. Thus, the likely explanation for the aberration from linearity and large y-intercepts for clam rennet is the presence of clam rennet inhibitor in milk. When the presence of inhibitor is taken into account, certain amount of clam rennet will be tied up by the inhibitors. The amount of clam rennet required to saturate the inhibitors is shown as the x-intercept. If data were replotted by subtracting this amount from the amount of clam rennet used, both equation 3-2 and equation 3-3 would have been closely followed by clam rennet. Certainly, equation 3-1 will also be followed, because both equation 3-2 and 3-3 degenerate to equation 3-1.

One more interesting observation was that clam rennet had higher clotting rate constant as indicated by the slopes of FIG. 7. The rate of constant of clam rennet is almost two times as high as those of porcine pepsin and calf rennet. Calf rennet and porcine pepsin have similar rate constants, likely due to their similar catalytic mechanisms. Both are carboxyl proteinases and preferably attach phe(105)-met(106) bond of κ-casein. Many proteolytic enzymes will induce clotting of milk, although this need not be taken as implying similarity in their mode of action to the carboxyl proteinases. Since the micellar instability is caused by the splitting of κ-casein in the region of 105-106 peptide bond, it may be assumed that any enzyme capable of hydrolyzing κ-casein at approximately this position should prove efficacious as a clotting agent (Dalgleish, 1982, supra). Clam rennet is a thiol proteinase, which tends to have broader specificity and attack several bonds at similar rates (Barrett, 1977b, supra). Thus, the relatively higher rate constant of clam rennet might result from its broader specificity.

TABLE 17

| | Linear regression parameters of | | | |
| Coagulant | Number of Observation | Slope | Intercepts X- | Intercepts Y- | Correlation coefficient ($R^2$) |
| --- | --- | --- | --- | --- | --- |
| Clam rennet | 8 | 0.11275 | 0.0234 | −0.00264 | .9972 |
| Porcine | 10 | 0.06597 | 0.0019 | −0.00013 | .9828 |

TABLE 17-continued

| | Linear regression parameters of | | | | |
|---|---|---|---|---|---|
| Coag- | Number of | | Intercepts | | Correlation coefficient |
| ulant | Observation | Slope | X- | Y- | ($R^2$) |
| pepsin | | | | | |
| Calf rennet | 10 | 0.06356 | 0.0014 | 0.00009 | .9775 | c. pH Effect on the Clotting Activity of Milk Coagulant

The influence of the pH of reconstituted milk powder on milk clotting times by different coagulants was studied. All three coagulant preparations had approximately equivalent activity at pH 6.2. The clotting activity of porcine pepsin decreased faster than the other two coagulants as pH increased. Porcine pepsin was unable to clot milk at pH 6.8 or above under the condition examined, likely due to the complete inactivation of the enzyme before the clot could be formed, since porcine pepsin is unstable at pH>6.0. Clam and calf rennet had similar pH profile of clotting activity. The clotting activity of all three coagulants appeared to be proportional to the logarithmic concentration of hydrogen ions, i.e. $(1/t_c) \alpha \log [H^+]$. The proportional rate constants reflect the pH optima of the coagulants. Porcine pepsin has lower pH optimum so that increase in hydrogen ion concentration is more likely to promote the action of porcine pepsin than clam or calf rennet.

d. Temperature Effect on the Clotting Activity of Milk Coagulant

The temperature dependence of milk clotting time for all three coagulants was studied. All three coagulants had similar clotting time in the temperature range from 30° to 37° C. Clam rennet appeared to be more active at higher temperature and porcine pepsin was least active at lower temperature.

The Arrhenius equation, $\kappa A e^{-E/RT}$, relates the rate constant $\kappa$ to activation energy E and absolute temperature T. A is the frequency factor and R is the gas constant. Since same amounts of coagulant were used for all temperatures, the change of milk clotting rate with temperature reflects the change of rate constant with temperature. Clam rennet more closely obeyed Arrhenius rule in the entire temperature range examined as indicated by its higher linear correlation coefficient. The increase of rate constants with temperature gradually declined for both calf rennet and porcine pepsin in high temperature region. This observation suggests that clam rennet is slightly more heat stable than the other two coagulants.

e. Curd Firmness and Cohesiveness

Firmness and cohesiveness of the clotted milk are affected by the type of milk coagulants along with many other factors, such as temperature, pH and calcium ion concentration. Calf rennet had highest initial rates for both cohesiveness and firmness. Porcine pepsin and clam rennet appeared to be inferior. There was substantial difference in curd firmness among all three coagulants 90 min after coagulation. However, the cohesiveness appeared to be identical for all three coagulants 90 min after coagulation despite the observation that the initial rates were different. The formation of softer curds by clam rennet and porcine pepsin is in agreement with the fact that both coagulants are more proteolytic than calf rennet. Although there is evidence which suggests that the rate of curd firming is not important in determining the properties of the curd, it is important to cut curd at the correct firmness so that the whey drains properly and the loss of milk solids is as low as possible (Green, 1977, supra). Thus, it would seem to be necessary to extend the clot-to-cut time when clam rennet or porcine pepsin is used as coagulant. This approach was used in the cheese-making trials as described above. However, the offset of this approach is that more proteolysis will occur and the loss of non-fat milk solids is still unavoidable. Addition of calcium chloride to increase curd firmness is a common practice of cheese industry to overcome this problem.

f. Calcium Ion Effect on Curd Firmness and Clotting Rate

It has long been established that the stability of casein micelles in milk is due to the stabilizing effect of κ-casein which protects whole casein micelles against flocculation by calcium ions. The clotting of milk by enzyme is initiated by specific enzymatic cleavage of the sensitive bonds of κ-casein and followed by the aggregation of the destabilized micelles. The aggregation stage is highly dependent on the presence of $Ca^{2+}$, thus an increase in calcium ions will bring about a reduction in coagulation time as well as an increase of curd firmness for all types of coagulants (Tofte Jespersen and Dinesen, 1979, supra).

Both curd firmness and clotting rate increased with increasing concentration of calcium chloride for every coagulant. Porcine pepsin appeared to be more sensitive to the concentration change of calcium chloride than either clam or calf rennet.

14. Cheddar Cheese from Clam and Calf Rennet a. Yield and Composition of Cheese

The percentage yield and composition of cheddar cheeses made from clam and calf rennets are shown in Table 18. After the adjustment of moisture, the yield of cheese from clam rennet was approximately 0.17% lower than from calf rennet.

Cheese yield may be influenced by fat loss, solids-non-fat loss and loss of curd fines (Tofte Jespersen and Dinesen, 1979, supra). A distinct relation between fat loss and type of coagulant used has not been reported in detail to any extent. However, loss of solids-non-fat is highly influenced by the proteolytic activity carried out by the coagulant used (Emmons and Beckett, 1977, supra). Thus, the reduced yield of clam cheese was likely caused by the coagulant's high proteolytic activity. This was consistent with the high levels of total and nonprotein nitrogen in whey (Table 19). High level of nonprotein nitrogen in clam cheese whey was partly attributable to the crude coagulant preparation, which containing 10 mM of cysteine used to activate the cathepsin B-line enzyme. This amount of nitrogen contributed by clam rennet was also detectable in the milk which was just renneted. The differences between total and nonprotein nitrogens in whey samples were similar for both coagulants. The fact implies that clam rennet has a s low activity toward whey proteins as calf rennet does. In commercial practice, the average level of total protein nitrogen in whey is 0.7–0.8% (Kosikowski, 1977, supra). High levels of total nitrogen in both whey samples reflected the relatively larger loss of curd fines from the small-scale cheese-making done in this study. The data should not be viewed as conclusive as more batches of cheese need to be made to obtain statistically relevant results regarding to the yield and composition of cheese made with clam rennet.

TABLE 18

Percent yield and composition of cheddar cheeses

| Coagulant | Yield | Composition | | |
|---|---|---|---|---|
| | | Moisture | Protein | Fat |
| Calf rennet | 10.19 | 37.03 | 25.16 | 33.75 |
| | (10.35) | (38.00) | (24.77) | (33.23) |
| Clam rennet | 10.19 | 38.08 | 24.13 | 33.75 |
| | (10.18) | (38.00) | (24.16) | (33.79) |

*The number in parentheses is adjusted to 38% moisture.

TABLE 19

Percent composition of renneted milk and whey

| Coagulant | Moisture | Fat | N × 6.38 | |
|---|---|---|---|---|
| | | | Total | Nonprotein |
| Renneted Milk | | | | |
| Calf rennet | 87.94 | 3.60 | 3.28 | 0.268 |
| Clam rennet | 87.93 | 3.60 | 3.31 | 0.296 |
| Whey | | | | |
| Calf rennet | 93.16 | 0.12 | 1.02 | 0.292 |
| Clam rennet | 93.14 | 0.12 | 1.16 | 0.441 | b. Cheese Ripening and Sensory Evaluation

Classical methods for following proteolysis during ripening of cheese depend upon measuring the increase of various forms of soluble nitrogen. However, it ws believed that total tyrosine liberated in aging cheese was a more sensitive criterion of ripening than the solbule nitrogen content (Silverman & Kosikowski, 1955 *J. Dairy Sci.*, 38: 941). Flavor intensity estimated by professional judges also showed a linear relationship to soluble tyrosine (Vakaleris and Price, 1959, supra). The amounts of soluble nitrogen, tyrosine and tryptophan in the extracts from both clam and calf cheese of different ages are shown in Table 20. Clam cheese was ripening much faster than calf cheese as indicated by all three parameters. The levels of soluble nitrogen, tyrosine and tryptophan in 2-week-old clam cheese were comparable to those of 8-week-old calf cheese. In 10-week-old clam cheese, these levels were compatible to those of 5 to 6-month-old calf cheese made by other investigators (Vakaleris and price, 1959; Shamsuzzaman and Haard, 1982).

TABLE 20

Soluble nitrogen, tyrosin and tryptophan contents of cheese extracts

| | Clam cheese extract | | | Calf cheese extract | | |
|---|---|---|---|---|---|---|
| Age (wks) | Soluble N ($A_{274.5}$) | Tyr (mM) | Trp (mM) | Soluble N ($A_{274.5}$) | Tyr (mM) | Trp (mM) |
| 2 | 0.798 | 0.186 | 0.115 | 0.480 | 0.085 | 0.075 |
| 4 | 0.894 | 0.251 | 0.115 | 0.548 | 0.120 | 0.080 |
| 6 | 1.068 | 0.290 | 0.138 | 0.654 | 0.148 | 0.094 |
| 8 | 1.238 | 0.349 | 0.155 | 0.762 | 0.167 | 0.110 |
| 10 | 1.504 | 0.435 | 0.184 | 0.888 | 0.251 | 0.114 |

Electrophoresis patterns of cheese have been used to compare the proteolytic action of milk coagulants on caseins (Mickelsen and Fish, 1970, *J. Dairy Sci.*, 53:704; Vanderpoorten and Weckx, 1972, supra). The electrophoretic patterns of cheeses at different ripening stages was studied. More proteolysis was obvious in clam cheese than calf cheese as indicated by the declination of color intensity of α- and β-caseins with age in two different cheeses. The color intensity of α- and β-caseins in two-week-old clam cheese was similar to 8-week-old calf cheese. The result was consistent with the soluble nitrogen, tyrosine and tryptophan contents. In calf cheese α-casein degradation proceeded faster than β-casein. Both caseins were degraded very fast by clam rennet. The degradation of α-casein in cheese made from microbial rennet tends to be relatively slow as compared with β-casein (Vanderpoorten and Weckx, 1972, supra).

The densitometer scanning of electrophoretic patterns of proteins from 2-week-old clam cheese and 8-week-old calf cheese were compared. Pattern similarity appeared to exist between these two samples. It is reasonable to believe that the cheeses which are organoleptically compatible shall have similar electrophoresis (or gel filtration) patterns. The sensory scores for 10-week-old cheeses are shown in Table 21. None of the pairs of treatments differ significantly at P<0.10 for any of the three attributes. However, all panelists indicated that they were able to realize the textural difference between clam and calf cheese. Clam cheese appeared to have more favorable flavor and acceptability scores than calf cheese despite the very slight bitterness detected by some panelists.

The extent of incorporation of active coagulant into cheese has been shown to be a function of the particular coagulant used (Holmes and Ernstrom, 1973, *J. Dairy Sci.*, 56: 622). In general, about 2–3% of the coagulant is contained in the curd as an active enzyme after processing, and it is this residual enzyme that assists in the ripening process. A current hypothesis for the process of flavor development is that a low redox potential has to be achieved within the cheese to allow chemical reactions to take place which result in the production of flavor components such as methanethiol (Manning, 1979, *J. Dairy Res.*, 46: 531). Microbial growth brings about a condition of low redox potential, and the more rapid and vigorous the growth, the quicker the ripening and flavor development are likely to be. Milk coagulants, by hydrolyzing some of the peptide bonds, degrades casein proteins to more assimilable fractions and thus encourage bacterial growth. As clam rennet is more proteolytic and has broader specificity than calf rennet, it is likely to produce more assimilable peptides to encourage microbial growth and accelerate the ripening process.

TABLE 21

Sensory evaluation scores[a] of 10-week-old cheeses

| Samples | Flavor | Texture and Body | Acceptability |
|---|---|---|---|
| Calf cheese-1 | 6.90 | 7.00 | 6.90 |
| Calf cheese-2 | 7.00 | 6.90 | 6.90 |
| Clam cheese-1 | 6.90[b] | 6.90 | 6.90 |
| Clam cheese-2 | 7.30[c] | 7.10 | 7.30 |

[a] 9 = like extremely and 1 = dislike extremely
[b] Bitterness detected by one out of ten panelists
[c] Bitterness detected by three out of ten panelists The choice of starter culture is important in flavor development. When large amounts of calf rennet were used to give increase proteolysis, fast acid starters produced bitter peptides while slow acid starters didn't (Lawrence, et al., 1972, supra); Lowrie and Lawrence, 1972, supra). It would be of interest and value to further investigate the effect of different starter cultures and/or coagulant amounts on the quality of cheese made from clam rennet.

15. Conclusions

Clam rennet, which is a crude enzyme preparation of cathepsin B-like proteinase found in clam viscera, was found to be suitable as a milk coagulant for cheese-making. The overall quality of cheddar cheese made from clam rennet was by no means inferior, if not superior, to cheddar cheese made from calf rennet. In some aspects, quality enhancement occurred despite that high ration of proteolytic to clotting activity was generally considered to be unfavorable for cheese-making. The higher proteolytic activity appeared to stimulate microbial growth and thus accelerated the ripening process. The small yield loss probably caused by rapid proteolysis during cheese-making might be offset by the economic advantage of a fast ripening process.

EXAMPLE 4

Evaluation of Clam Viscera Proteinase as Meat Tenderizers

Of all the quality attributes of meat, it is appearance which largely determines consumer selection or rejection of meat at the time of purchase. Appearance, however, is often unrelated to the eating quality. Tenderness has been rated as the most important quality attribute by the average consumer. It is defined as that quality of cooked meat that is recognized by the characteristic of easy chewability without loss of desirable texture (Bernholdt, 1975, *Enzymes in Food Processing*, Reed, ed., Acad. Press, N.Y., 473). All segments of the livestock and meat industry, along with the consumer, have striven for may years to achieve this attribute. Various methods of improved breeding, improved feeding, post-mortem aging, grinding and even the addition of artificial enzyme preparations have been used to induce meat tenderness. The mechanism of meat tenderization process has not been completely elucidated. However, recent developments in meat science have demonstrated that the endogenous proteolytic enzymes of muscle tissues play an important role in the post-mortem meat tenderization process. These enzymes include calcium-activated neutral proteinase (CANP) and lysosomal catheptic enzymes B and D (Dransfield and Etherington, 1981, *Enzymes and Food Processing*, Birch et al., eds., Appl. Sci. Publ, London 177). In view of this observation, a brief study was undertaken to investigate the feasibility of accelerating meat tenderization process by the application of B- and D-like cathepsins isolated from clam viscera.

1. The Effect of Post-Mortem Handling on Meat Tenderness

In living muscle the ATP is constantly turned over to maintain the metabolism and the pH of the muscle approximates a value of 6.7 to 7.2. When the oxygen supply is withdrawn at slaughter, ATP is consumed in an attempt to maintain temperature and cell integrity. The loss of ATP triggers off anaerobic conversion of glycogen to lactic acid with the result that after 24 hours the pH of the muscle generally falls to 5.5 (Penny, 1980, *Dev. Meat Sci.*, 1: 115). Both the rate and extent of post-mortem glycolysis affect the tenderness of the cooked meat. With adequate initial concentrations of glycogen, the factor that limits the extent of glycolysis is pH. When pH gets low enough certain critical enzymes, especially fructokinase, are inhibited and glycolysis ceases. If an animal prior to slaughter is stressed or exercised vigorously its glycogen content is decreased substantially and higher ultimate pH is likely to result post-mortem. This phenomenum commonly occurs with fish muscle since fish often struggle vigorously during harvest and prior to death. The ultimate pH that is attained has an important influence on the textural quality of meat, its water holding capacity, its resistance to microorganisms and its color. High pH meat is very subject to microbial spoilage and tends to be very dark in color, firm and dry and is unacceptable in appearance to consumer at retail outlets (Morrisey and Fox, 1981, *Irish J. Food Sci. & Tech.*, 5: 33).

The rate of glycolysis or pH drop is affected by such factors as species, type of muscle, individual variation among animals, and temperature of the carcass. A too rapid drop in pH post-mortem combined with high temperature of carcass soon after slaughter causes denaturation and precipitation of the sarcoplasmic proteins onto the myofibrils and lead to a condition known as pale, soft and exudative (PSE) meat that is especially common in pork.

Post-mortem handling of meat is now recognized to cause a large variation in meat tenderness. In commerce, rapid chilling of carcass is attractive because it reduces evaporative weight loss, retards microbial growth and allows an increased throughput of animals slaughtered. However, cold-shortening of the muscle occurs and leads to a considerable toughening of the meat. The shortening is a result of the muscle contraction while there is still abundant ATP remaining. The most promising way to avoid toughening due to rapid chilling is electrical stimulation of carcass. A considerable amount of work has been devoted to the mechanism by which tenderness is increased by electrical stimulation. The theories include the prevention of cold shortening (Crystal and Hagyard, 1976, *N.Z. J. Agri. Res.*, 19: 7), physical disruption of muscle fibers (Savell et al., 1978, *J. Food Sci.*, 43: 1606) and increased proteolytic activity by natural enzymes. However, at the present time the information about the process indicates that the rapid decrease in pH of electrically stimulated muscle while the carcass is still near the in vivo temperature may induce and enhance the catheptic enzyme activity. The enhanced proteolysis by catheptic enzymes might thus increase the tenderness of electrically stimulated muscle (Morrisey and Fox, 1981, supra).

It is often recommended that beef should be conditioned at 2° C. for 10 days, but this is rarely achieved in practice. Increasing the storage temperature increases the rate of tenderizing. Accelerated tenderizing is observed at temperature up to 60° C. (Davey and Gilbert, 1976, *J. Sci. Food & Agric.*, 27: 244), indicating considerable thermal stability of the enzymes involved. However, a special process (Tenderay process), which calls for a special room equipped with ozone generating ultraviolet lamps and constant circulation of purified and humidified air to inhibit microbial growth and prevent evaporated weight loss, is required for accelerated tenderizing. Tenderization didn't occur during frozen storage although it does commence on thawing. Cycles of freezing and thawing have not been found to affect the rate of tenderizing (Locker and Daines, 1973, *J. Sci. Food & Agric.*, 24: 1273).

2. The action of endogenous muscle proteinases in meat conditioning

Meat is a complex product composed chiefly of skeletal muscle tissue together with connective and fatty tissues. While fat does contribute to tenderness, it mostly contributes to flavor than to tenderness. The main structures affecting meat tenderness are connective tissues and the muscle myofibrils. Since both tissues are almost exclusively proteinaceous structures, the proteinases are of particular importance in meat conditioning.

a. Calcium-activated neutral proteinase (CANP)

The observations of Busch and co-workers (1972, *J. Cell Biol.*, 52: 367) that the rigor tension of muscle fell more rapidly during storage in a medium containing 1 mM $Ca^{2+}$ than in one with EDTA led to the discovery of a muscle protease which was activated by calcium ion. The enzyme has been called calcium-activated factor—CAF (Dayton et al., 1976, *Biochemistry*, 15: 2150) and calcium-activated neutral proteinase—CANP (Ishiura et al., 1978, *J. Biochem.*, 84: 225). The latter is the most accurate description of the enzyme but the trivial name CAF is now generally accepted. The enzyme has been purified from pig muscle by Dayton and co-workers (1976, supra). The yield was only 0.4 mg/Kg but they calculated the total amount of enzyme in the muscle to be about 3 mg/Kg. Calcium-activated proteases that are similar, if not identical, to the skeletal muscle CANP have been isolated from brain (Inoe et al., 1978, *J. Biolog. Chem.*, 252: 7610), calf uterus (Puca et al., 1977, *J. Biolog. Chem.*, 252: 1358), platelets (Philips and Jakabova, 1977, *J. Biolog. Chem.*, 252: 5602) and hen oviduct (Vedeckis et al., 1980, *Biochemistry*, 19: 335).

Most workers are in agreement that CANP removes z-disks during post-mortem storage (Dayton et al., 1976, supra; Azana et al., 1979, *Biochem. J.*, 183: 339; Olson et al., 1977, *J. Food Sci.*, 42: 117). However, the mode of action of the enzyme has remained in doubt, because the major proteins of z-disk, α-actinnin, is not itself susceptible. Purified CANP has also been shown to hydrolyze Troponin T and I, tropomyosin, M-protein and C-protein in the myofibrils. However, actin, myosin, troponin C and α-actinnin are resistant to proteolysis by CANP. The CANP treated meat was significantly more tender than meat with no added enzyme (Penny et al., 1974, *J. Sci. Food & Agric.*, 25: 703.

b. Cathepsins B and D

Although considerable amounts of effort have been devoted to showing that CANP is involved in the meat conditioning process, catheptic enzymes had been implicated in this process long before CANP was discovered. Cathepsins B and D have been prepared from a wide variety of tissues, liver being the most common source. These two enzymes are also found in skeletal muscle, but yields of cathepsins B and D are about 2 to 3% of those from liver. It has been calculated that skeletal muscle contains about 2-3 mg of cathepsin D and about 1 mg of cathepsin B per kilogramme. Cathepsin B is a thiol proteinase requiring sulphydryl reducing agents for activity and is inhibited by iodoacetate, heavy metals and leupeptin (Barrett, 1977b, supra). The addition of EDTA to chelate heavy metals is necessary in order to obtain maximum activity. Cathepsin D doesn't require activators and is inhibited by pepstatin (Barrett, 1977c, supra).

Most of the information about cathepsins B and D in meat has come from studies on the action of the purified enzymes on specific myofibrillar components. Eino and Stanley (1973, *J. Food Sci.*, 38: 45 and 51) observed that a preparation of muscle cathepsin D incubated with myofibrils under post-mortem pH conditions produced structural changes similar to those observed during conditioning of muscle. Robbins and Cohen (1976, *J. Texture Studies*, 7: 137) treated bovine myofibrils at pH 5.3 with an extract of bovine spleen which contained a high concentration of cathepsin D in addition to other catheptic enzymes. They found selective degradation at the z-disk zone in addition to some breakdown of the sarcolemma and stoma proteins. Arkawa and co-workers (1976, *Agric. & Biolog. Chem.*, 40: 1265) reported that a catheptic enzyme preparation obtained from rabbit muscle, probably cathepsin B, degraded heavy chain myosin. Catheptic enzymes were further implicated in meat tenderness by the work of Moeller and co-workers (1976, 1977, *J. Food Sci.*, 41: 216 and 42: 510). They found that under high temperature conditioning, which produces a more rapid post-mortem pH decline, lysosomal membranes were disrupted as evidenced by a significant increase in the activity of lysosomal enzymes, cathepsin C and β-glucuronidase, in the soluble protein fraction of meat homogenates. Although the release of cathepsin B and D has not been specifically demonstrated, both may be expected to follow the same pattern as other lysosomal enzymes.

c. The relative importance of CANP and cathepsins

There are several unresolved questions on the relative importance of CANP and cathepsins in conditioning meat. Both CANP (Penney, 1980, supra) and cathepsins (Morrissey and Fox, 1981, supra) have been claimed as the most important factor responsible for the post-mortem meat tenderization. CANP appeared to be the enzyme most likely to be involved because its activation by calcium ions explains the accelerating effect of $Ca^{2+}$ ions on conditioning and it can mimic the changes observed during conditioning. However, the high pH optimum of CANP (7.5-8.0) reduces the possibility that the enzyme plays a significant role in myofibril breakdown under post-mortem conditions. Furthermore, from in vitro experiments CANP is activated by millimolar levels of $Ca^{2+}$ ions. This is far in excess of the sarcoplasmic level in the living animal cell which is in the order of $10^{-8}$–$10^{-6}$ M or in post-mortem myofibril cell which is $\sim 10^{-5}$ M. Thus, some other, as yet unidentified, activating agent must be present in muscle to alter the $Ca^{2+}$ requirements if this enzyme is to function during conditioning. More recently, a low-calcium-requiring form of CANP has been isolated and purified from skeletal muscle (Dayton et al., 1981, *Biochem. et Biophysica Acta*, 659: 48). This enzyme requires only micromolar levels of $Ca^{2+}$ ions for detectable activity and retains significant activity at pH as low as 5.5. Therefore, it might be this form of CANP that is active in vivo.

Research workers in both electrical stimulation (Dutson et al., 1979, *J. Food Sci.*, 45: 1097) and high temperature conditioning (Moeller et al., 1976, 1977, supra) have shown that lysosomal enzymes are extensively released into the cytoplasm under these conditions and they proposed that tenderness is related to the increased catheptic activity. However, in a muscle with a low CANP concentration but containing cathepsins, proteolytic breakdown of myofibril is not observed during traditional conditioning (Olson et al., 1971, supra).

From these observations, it appears that CANP may initiate degradation at the z-disk during the first 4-5 hours post-mortem while the pH is still greater than 6.0.

At the same time, the production of lactic acid through anaerobic glycolysis brings the pH of the muscle towards its final value of 5.5. Further changes would then be elaborated by the catheptic enzymes which are subsequentially released due to membrane disintegration as pH declines.

3. Artificial meat tenderization

Because natural conditioning of meat is unlikely to make the meat from older animals fully acceptable to the consumer, it's reasonable to believe that artificial tenderizers have an attractive role in augmenting the action of muscle proteinases. The Mexican Indians have known for about 400 years that the latex from papaya leaves has a tenderizing action on meat during cooking. However, the use of exogenous enzymes to upgrade poor quality cuts of meat was first practiced on a commercial basis in 1949 (Whitaker, 1959, *Adv. Food Res.*, 9: 1). In 1973 between 30–40% of the world's meat supply was artificially tenderized and such treatment increased the percentage of a carcass saleable as prime cuts from 10 to 70% (Fox, 1973, *J. Dairy Res.*, 36: 427).

The proteolytic enzymes used fall into three main categories according to sources (Morrissey and Fox, 1981, supra):
(1) plant: bromelain, ficin, papain
(2) animal: trypsin, chymotrypsin, Viokase (a defatted and desiccated porcine pancreas powder)
(3) Bacterial and Fungal: Rhozyme P-11, Protease-15, subtilisin and Pronase Papain is the main enzyme of commercial interest, probably due to its relatively low cost combined with the fact that it is a plant enzyme and deemed safe as a food additive.

The tenderizing enzymes can be applied either ante-mortem or post-mortem. Only those enzymes that can be reversibly inactivated could be used ante-mortem, because direct injection of a large dose of active enzyme into the circulation system of a living animal will cause severe shock, followed rapidly by hemorrhage and then death. Thiol-proteinases appear to be the most convenient and effective for ante-mortem treatment, because continuing glycolysis post-mortem depletes the muscle of oxygen with the result that oxidized thiol proteinase become reactivated by the accumulated free thiols and other reducing agents. The most successful ante-mortem process is the Proten process developed by Swift and Company Limited, Chicago, IL (Warner et al., 1976, British Patent No. 1,448,498). In this process a concentrated solution of papain is injected into the jugular vein ten to thirty minutes before slaughter at a dose-rate of 2–5 ppm. This process utilizes the heart and vascular system for enzyme distribution, thus permits an even distribution of enzyme in the muscle. However, the commercial value of the edible offals may be reduced by overtenderization due to their highly vascular nature. Most recently a new patent (Kang et al., 1982, U.S. Pat. No. 4,336,271), which accelerates the natural tenderization process by ante-mortem injection of selected enzyme activators and/or binding agents of enzyme inhibitors naturally present in meat, has been issued to the same company. The solution to be injected into live poultry/animals comprises an aqueous solution of an unionized Calcium salt and a zinc chelating compound.

The direct application of proteolytic enzymes post-mortem provides some degree of tenderness. Thin steaks can be dusted, dipped or sprayed with an enzyme solution, but for larger pieces, such as primal joints, the enzymatic preparation must be injected using an aqueous or gaseous carrier. There are some disadvantages to post-mortem tenderization, including lack of uniformity in the application of the meat, and the fact that surface granulation or mushiness often occurs.

4. Enzymatic preparations and treatments

The crude extract from clam viscera was acidified and concentrated according to the methods described in Example 3 for the preparation of clam rennet. The ultrafiltration retentate was then fractionated with ethanol to obtain either 40–70% or 55–70% fraction. The 40–70% ethanol fraction contains both B-like and D-like cathepsins with a relative activity ratio of B-like to D-like cathepsin approximating 36:64 at pH 2.8 when hemoglobin was used as substrate (see Table 14). These fractions were reconstituted in 0.05 M citrate-phosphate buffer containing 0.0005 M cysteine-HCl with final pH 5.6 to predetermined levels of proteolytic activity at pH 2.8 using casein as substrate. Total proteolytic activity was determined according to the method described in Example 1. Same buffer solutions with or without cysteine were used as controls. One-inch-thick rib steaks, which were removed 24 hour post-mortem from two dairy cow in Cornell Dairy herd, were selected so that equal number of ribs from each side of the animal were assigned to same group of treatments. The first cow, #2662, was born on July 31, 1975 and the second one, #1538, was born on Dec. 18, 1977. This study was conducted in May, 1984. Each rib steak was treated with 300 ml of solution in a sterile Whirl-pak bag for predetermined time period at predetermined temperature. In some cases, rib steaks were freeze-dried in a Stokes freeze-drying equipment, Model 2004-LX3 (F.J. Stokes Machine Co., Philadelphia, PA), for 2 days before treatment.

5. Shear force determination and sensory evaluation

Treated steaks were roasted to an internal temperature of 70° C. in a 176.7° C. forced-air convention oven (Blodgett Inc., Model EF111, Birminghan, VT). The temperature was monitored by the Omegaline thermal couple and temperature recorder (Omega Engineering Inc., Stamford, CT). For each roasted steak, one strip of sample ($\sim 1.27 \times 8$ cm) was taken from both sides of the center 2.54-cm-wide strip in the direction of the muscle fibers, wrapped in aluminum foil and kept warm in a 40° C. incubator. These two strips were then cut into 8 pieces in cross-section immediately before being given to 4 panelists, two for each. The panelists were asked to score the tenderness, juiciness and the amount of connective tissue from different steaks (test with scale similar to described in Example 3). Three 1.27-cm cores were removed from cooled 2.54-cm-wide center strip and each core was sheared three times on a Warner-Bratzler shear device to measure the toughness of the samples.

6. Results

The effect of different treatments on the tenderness of rib steaks from the carcass of an 8-year-old cow is shown in Table 21. The toughness appeared to have been reduced when steaks were treated at 25° C. for 50 min using either 40–70% or 55–70% ETOH fraction with a total activity of 100 CU/ml. Similar results were obtained for freeze-dried steaks reconstituted for 3 days at 2° C. using a total activity of 13.2 CU/ml. Incomplete rehydration was observed when steaks were only rehydrated for one day, likely due to the entrapped air which prevented the free movement of solution. The differences between every pair of treatment, however, were not significant except the pair of control without cysteine and 40–70% ETOH fraction. Furthermore, no statistically significant results could be found from the sensory scores. It was suspected that the inability of the panelists to find the difference was caused by insufficient treatment or by the high background toughness of connective tissues which is characteristic of old animals.

The effect of prolonged treatment using a younger cow is shown in Table 22. Similar patterns were observed in both 10° C. and 20° C. treatments. There were obvious differences between samples such as those treated with control without cysteine and sample treated with 40–70% ETOH fraction as indicated by the P values. The difference between samples treated with control with cysteine and 40–70% ETOH fraction appeared to be less than the previous difference. This observation suggests that cysteine might activate the endogenous cathepsins, despite the fact that there was no significant difference between control without cysteine and with cysteine. No significant difference was observed between 55–70% ETOH fraction and control with cysteine, indicating that D-like enzyme has minimum role in the tenderizing process. It appeared that tenderness difference was more likely to be detected by panelists when there was very significant difference in shear force. Another observation was that juiciness didn't appear to correlate with tenderness as connective tissue did. High juiciness scores were likely due to the prolonged treatment of samples in solutions.

TABLE 22

Tenderization of rib steaks from the carcass of an 8-year-old cow using different treatments

| Treatment | Shear force$^a$ (kg) | | |
|---|---|---|---|
| temperature | 25° C. | 25° C. | 2° C.$^b$ |
| time | 10 min | 50 min | 3 days |
| total activity | 100 CU/ml | 100 CU/ml | 13.2 CU/ml |
| Control w/o cysteine | 6.87 | 7.04 | 6.60 |
| Control w/ cysteine | 6.89 | 6.43 | 6.24 |
| 40–70% ETOH fraction | 7.22 | 5.10$^c$ | 5.19$^c$ |
| 55–70% ETOH fraction | 7.10 | 5.87 | 5.87 |

$^a$Each value represents the mean force of 9 replicates to shear a 1.27-cm core.
$^b$Freeze-dried sample
$^c$Differ significantly from control w/o cysteine in same column at $P < 0.05$.

7. Conclusions

This investigation demonstrated that steak tenderness could be improved by using the proteinases isolated from clam viscera as tenderizing agents. Cathepsin B-like enzyme played a major role while cathespin D-like enzyme was slightly active under the conditions studied.

TABLE 23

Tenderization of rib steaks from the carcass of a 6-year-old cow by different treatments

| | Treatment | | | | | | | |
|---|---|---|---|---|---|---|---|---|
| temperature time total activity | 20° C. 20 hrs 40 CU/ml | | | | 10° C. 20 hrs 40 CU/ml | | | |
| | Shear force (kg) | Tenderness | Juiciness | Connective tissue | Shear force (kg) | Tenderness | Juiciness | Connective tissue |
| A Control w/o cysteine | 6.30 | 3.75 | 6.00 | 3.00 | 6.05 | 4.25 | 5.75 | 3.00 |
| difference btwn A,B | n.s. | n.s. | n.s. | n.s. | n.s. | n.s. | n.s. | — |
| difference btwn A,C | *** | *** | n.s. | * | *** | *** | n.s. | — |
| difference btwn A,D | * | n.s. | n.s. | n.s. | * | n.s. | n.s. | — |
| B Control w/ cysteine | 5.49 | 5.00 | 5.75 | 2.25 | 5.47 | 4.75 | 5.75 | 2.75 |
| difference btwn B,C | ** | n.s. | n.s. | n.s. | ** | ** | n.s. | ** |
| difference btwn B,D | n.s. | n.s. | n.s. | n.s. | n.s. | n.s. | n.s. | n.s. |
| C 40–70% ETOH fraction | 3.78 | 6.25 | 6.25 | 1.75 | 4.14 | 6.25 | 6.75 | 1.50 |
| difference btwn C,D | * | n.s. | n.s. | n.s. | n.s. | n.s. | n.s. | n.s. |
| D 55–70% ETOH fraction | 4.70 | 5.25 | 5.75 | 2.25 | 4.78 | 5.50 | 6.25 | 2.00 | n.s. not significant;
***significant at $P < 0.01$;
**significant at $P < 0.05$;
*significant at $P < 0.1$
— unable to compute due to all scores for that sample were identical

EXAMPLE 5

Process Optimization for the Concentration and Fractionation of Clam Viscera Proteinases by Ultrafiltration An integral stage of the production of enzyme preparations for industrial and other large scale uses includes in most cases concentration and purification by such methods as vacuum evaporation, adsorption on specific carriers and precipitation with organic solvents or salts. These methods can expose delicate enzymes to high temperatures or physico-chemical changes to alter the properties of the enzyme molecule, leading to appreciable losses of enzymatic activity (Walliander et al., 1975, *Kemia-Kemie*, 2:373).

The use of ultrafiltration not only enables one to concentrate enzymes, but during the concentration procedure an array of contaminating salts and small molecules can also be removed. In addition, the energy requirements in ultrafiltration per volume of water removed are substantially lower than most systems including those in evaporation. This technology is of increasing interests in the purification and concentration of various enzymes (Butterworth and Wang, 1972, *Ferment. Tech. Today*, Tervi, ed., Soc. Ferment. Tech., Japan, 195: Shishkova et al., 1981, *Appl. Biochem & Microbiol.*, 17: 172: Rassulin, et al., 1981, *Appl. Biochem & Microbiol.*, 17: 176).

Considerable amounts of effort have gone into the development of ultrafiltration concepts and theories by examining the behavior of ultrafiltration process using pure enzyme or protein solutions. However, some of these theories may not be applicable to the ultrafiltration of heterogenic crude enzyme preparations. The properties of the solution very much affect the behavior of the ultrafiltration process in addition to the fact that special care must be taken to protect the enzymes of interest from losing activity. Thus, the objective of this part of the work was to experimentally select the optimum operational parameters for the concentration and-/or purification of clam viscera extracts by means of ultrafiltration.

1. Specific concerns related to enzyme concentration and purification

In evaluating the feasibility of using ultrafiltration to concentrate and/or purify enzyme streams, the following factors must be considered:

a. Recovery of enzyme activity

Ultrafiltration membranes with nominal molecular weight exclusion limits in the range of 10,000–20,000 are normally used for enzyme processing. With such membranes, enzyme activity losses in the ultrafiltration normally do not exceed 2–4% of the feed activity. The activity recovery in the combined concentrate and permeate streams is typically 95–100% of that in the feed stream. By way of comparison, activity recoveries in vacuum evaporation systems are reported to lie in the 60–90% range. The small apparent activity losses in ultrafiltration systems have been variously attributed to such phenomena as (i) shear inactivation associated with pumping, (ii) degradation due to microbial contamination, (iii) adsorption losses on the membrane surface, and (iv) inactivation due to changes in ionic environment (Beaton, 1980, *Ultra. Filt. Memb. & Appl.*, Cooper, ed., Plenum Press. NY, 373). Among other possibilities are thermal inactivation and, in the cases of proteinases, autodegradation. The extent to which enzyme inactivation takes place by a particular mechanism is highly dependent on enzyme type and if the mechanism can be identified, methods are often available for reducing or even eliminating the loss of activity. For examples, positive-displacement pumps can replace the centrifugal pumps to handle very shear-sensitive enzyme streams. Loss of activity due to autodegradation, microbial degradation and thermal inactivation can be minimized by operating at low temperatures or by the reduction of process cycle period.

b. Degree of concentration and purification

Since the enzyme is almost totally retained by the membrane, the purity (specificity) of the retentate increases during ultrafiltration. The degree of enzyme purification achievable directly by means of ultrafiltration is restricted by the degree of concentration economically attainable due to the gradual decrease in membrane flux during ultrafiltration. Volume reduction factors in the range of 10–50 folds are typical (Beaton, 1980, supra). Further purification is possible through use of the diafiltration procedure involving addition of water (buffer) to the retentate stream. However, the value of the improved enzyme purity associated with diafiltration must be balanced against increased ultrafiltration costs incurred by the additional membrane area required to accomplish the task within the same process time.

c. More than one enzyme

When feed stream contains more than one enzyme, it would be of great advantage to the ultrafiltration process if these enzymes can be fractionated while the feed stream is being concentrated. Due to concentration polarization and membrane fouling, the use of this tool for efficient fractionation of proteins according to size is unlikely unless they differ by a factor of ten in their molecular weights. However, through the selective manipulation of feed properties such as ionic strength the fractionation of proteins with closer molecular weight might be feasible due to the shift of balance in protein-protein interactions (Ingham et al., 1980, *Ultrafilt. Memb. & Appl. supra*, 141). Another approach might be to add fully rejected ligands which reversibly and selectively bind to one of the enzyme, For example, better separation of trypsin and peroxidase by ultrafiltration can be achieved by using crosslinked soybean trypsin inhibitor (Bartling and Barker, 1976, *Biotech. & Bioengin.*, 18: 1023).

2. Preparation of acidified clam viscera extract

Clam viscera extract was prepared and acidified according to the method describes in Example 3. Acidification was considered to be a necessary pretreatment step to remove most undesirable materials, because excessive membrane fouling occurred when crude clam viscera extract was used as feed solution. Among all the preparations used in this study, the total solids and protein contents were in the range of 2.80–309 and 0.075–0.104%, respectively, and the D-like and B-like activity were in the range of 32.0–44.5 and 48.0–66.8 CU/ml, respectively.

3. Protein concentration determination

The determination of protein concentration was carried out according to the method described in Example 1.

4. Total solids determination

The content of total solids was determined by drying 2 ml of sample in an atmospheric oven set at 102° C. for 24 hrs.

5. Proteolytic activity determination

To determine the total activity, the buffer used was 0.2 M citrate-phosphate solution of pH 2.8 containing 10 mM of cysteine-HCl which served as the activator of B-like cathepsin. Same citrate-phosphate solution without cysteine-HCl but with 1 mM $CuCl_2$, which served as an inhibitor of B-like cathepsin, was used to determine the D-like activity. B-like activity was calculated from the difference between total and D-like activity. Procedure similar to the one described in Example 1 was followed except that enzyme solution was preincubated with buffer solution for 10 min at room temperature to allow the completion of activation or inhibition of B-like cathepsin.

6. Ultrafiltration

Ultrafiltration studies were carried out with Amicon thin-channel ultrafiltration system, model TCF-10 (Amicon Corporation, Lexington, MA). Unless otherwise mentioned, the system equipped with a PM30 membrane was operated at 35 psig in a 2° C. cold room with a recirculation rate of 200 ml/hr to concentrate and fractionate batchwise 500 ml of feed solution until 450 ml (including 3 ml hold-up volume) of permeate was collected. If necessary, the pH of the feed solution was adjusted with 2 N HCl or NaOH, the pressure was regulated by pressurized nitrogen tank and the recirculation rate was adjusted by the speed of the integral peristaltic pump. Used membranes were cleaned after each run by soaking the membranes at 50° C. overnight in 0.1% Abcor Ultraclean II solution (Abcor Inc., Wilmington, MA) with pH adjusted to 11–12, then rinsed throughly with distilled water.

The instantaneous fluxs at different intervals of each ultrafiltration run were determined by timing the collection of 5 ml of permeate. The rejection of any solute by a specified membrane under specified conditions was expressed by the rejection coefficient, R, which is defined as in the following equation:

$$R = 1 - C_u/C_f \qquad \text{(eq. 5-2)}$$

where $C_u$ is the solute concentration in the ultrafiltrate and $C_f$ is the solute concentration of the feed solution. From the mass balance, $C_u$ can be expressed as following:

$$C_u = (C_f V_f - C_r V_r)/V_u \qquad \text{(eq. 5-3)}$$

where $C_r$ is the solute concentration in the retentate, $V_f$, $V_r$, and $V_u$ are volumes of feed solution, retentate and ultrafiltrate, respectively. By substituting of equation 5-2 into equation 5-3 and rearranging, the following equation is obtained:

$$R = 1 - (V_f/V_u) + (C_r V_r/C_f V_u) \qquad \text{(eq. 5-4)}$$

In calculating rejection coefficient, equation 5-4 was preferred to equation 5-2 due to the relatively large inaccuracy in determining the extremely low proteolytic activity and protein concentration in the ultrafiltrate.

7. Results

Two important ultrafiltration process parameters, solute rejection coefficient and permeate flux, are to be discussed. The former influences the recovery and purity of the enzyme, and the latter influences the operational and capital costs.

8. Membrane selection and temperature effect

Three types of highly water-permeable Amicon membranes, XM50, PM30 and PM10, were investigated for their suitability in concentrating and/or fractionating B-like and D-like cathepsins. Some important properties of these membranes are summarized in Table 24. PM10 and PM30 membranes, which are polysulfone in nature, have higher water permeability than acrylic XM50 membrane despite that the latter has larger pore diameter.

TABLE 24

| | Select properties of different Amicon membranes | | |
|---|---|---|---|
| Membrane | Deionized water flux (ml/cm²/min) | Molecular-weight-Cut-off | Approximate pore size (nm) |
| XM50 | 1.0–1.8 | 50,000 | 3.1 |
| PM30 | 5.0–10.0 | 30,000 | 2.2 |

TABLE 24-continued

| | Select properties of different Amicon membranes | | |
|---|---|---|---|
| Membrane | Deionized water flux (ml/cm²/min) | Molecular-weight-Cut-off | Approximate pore size (nm) |
| PM10 | 2.5–4.0 | 10,000 | 1.6 |

*source: Ultrafiltration and Microporus Filtration Catalog, Publication No. 550, Amicon Corporation.

The rejection of solids, proteins, B-like and D-like cathepsins by these membranes at two different temperatures are shown in Table 25. All types of solutes examined appeared to be less permeable at lower temperature regardless of the membrane types, likely due to membrane pore contraction at lower temperature. Similar results were observed in the ultrafiltration of skim milk under refrigerated conditions (Kapsimalis and Zall, 1981, *J. Dairy Sci.*, 64: 1945). The rejection coefficients for each solute decreased with increased molecular-weight-cut-off (pore size) of the membranes. B-like cathepsin is less retainable than D-like cathepsin due to the molecular weight of the former (~17,400) is less than the latter (~36,700). However, the rejectivity of both B-like and D-like cathepsins were relatively high, especially at low temperature, even though the molecular weights of these enzymes are well below the exclusion limits of PM30 and XM50 membranes, respectively. One explanation is that the presence of large amounts of low molecular weight substances in the clam viscera extract might have enhanced the interactions between these enzymes and other macromolecules or perhaps a self-association of the enzymes occurs whereby the existence of specific effectors (usually salts) can frequently affect the interactions between protein molecules (Koshland, 1970, *The Enzymes*, Boyce, ed., 3rd ed., 1: 341; Frieden, 1971, *Ann. Rev. Biochem.*, 40: 653). Furthermore, many macromolecules are in concentration-dependent self-association equilibrium. Due to concentration polarization the effective molecular size at the membrane surface may be much larger than the native molecule and increased rejection of 'presumed' permeable species may thus be observed (Jeffrey, 1974, *Biochemistry*, 13: 4441). Both the recovery and purity of enzymes are interrelated to rejection coefficient. Higher rejection coefficient indicates higher recovery for the enzyme. The purity factor achieved by ultrafiltration on the basis of total solids is several times higher than on the basis of protein as indicated by their relative magnitudes of rejection coefficients.

Based on the assumption that all solutes are either free permeable or totally retainable and the flux is dependent on membrane retainable species, the gel polarization model of equation 5-1 can be expressed as following:

$$J = K_s \ln (C_g/C_f) - K_s \ln (V_f/V_r) \qquad \text{(eq. 5-5)}$$

where all symbols bear the same meaning described earlier. If $K_s$, $C_g$ and $C_f$ are constants, a semilog plot of volume reduction factor, $V_f/V_r$, vs. flux, J, will generate a straight line. The slope of the line indicates the magnitude of apparent mass transfer coefficient and the intercept on x-axis indicates the logarithmic ratio of apparent gel concentration and initial macrosolute concentration.

TABLE 25

The effect of membrane type and temperature on solute rejection of acidified clam viscera extract

| Membrane | Temperature (°C.) | % Rejection | | | |
|---|---|---|---|---|---|
| | | Solids | Proteins | Cathepsins D-like | Cathepsins B-like |
| XM50 | 2 | 5.98 | 56.14 | 95.37 | 78.79 |
| PM30 | 2 | 6.23 | 57.78 | 99.93** | 84.20 |
| PM10 | 2 | 7.85 | 61.56 | 101.72 | 95.36 |
| XM50 | 20* | 3.40 | 41.78 | 67.84 | 65.15 |
| PM30 | 20 | 4.45 | 45.61 | 88.12 | 72.76 |
| PM10 | 20 | 5.39 | 49.95 | 91.45 | 79.85 |

*Room temperature. The temperature of the retentate increased towards the end of the run.
**Due perhaps to the inaccuracy of the proteolytic assay.

As shown in FIG. 8, disregard of the membrane types and temperatures the ultrafiltration flux declination was nonlinear, with a sharp decline initially followed by steady declination after about 2 times reduction of initial volume. This observation suggests that no gel layer was formed initially and the apparent mass transfer coefficient was high as indicated by the slope of the initial stage. However, as the concentration polarization aggravates rapidly during this stage, the accumulation of macrosolutes on membrane surface leads to the gradual decline of the apparent mass transfer coefficient until the onset of a macrosolute gel layer where apparent mass transfer coefficient becomes constant and the flux becomes dependent only on the bulk concentration, or, in this case, volumetric concentration factor. For each membrane higher flux was obtained at higher temperature due to decreased fluid viscosity which leads to a reduction in boundary layer thickness and increase i solute diffusivity. The flux of ultrafiltering acidified clam viscera extract was such lower than the pure water flux for each type of membrane. All lines appeared to converge to x-axis, indicating that temperature and membrane type didn't affect the gel concentration significantly. Similar result was observed when animal blood was ultrafiltered (Fernando, 1981, *Biotech. & Bioengin.*, 23: 19).

PM30 membrane was subjectively selected for further investigation, because this membrane was shown to be more hydraulic permeable with reasonable recovery of the activity of both enzymes. Due to poor temperature control when the ultrafiltration system was operated at room temperature, further operations were conducted in a 2° C. cold room.

9. The effect of pH

It is well known that pH of the solution significantly influences the solubility and conformation of protein molecules. For example, at the isoelectric point the solubility of protein is, in general, minimum and the agglomerating tendency is maximum. In addition, protein/membrane interaction is likely to be pH dependent. Thus, the rejection coefficient and solvent flux are expected to be a strong function of the solution pH. The effect of feed pH on the solute rejection of acidified clam viscera extract is shown in Table 26. It appeared that less solids and proteins were retained at lower pH. One likely explanation is that lowering the pH reduces the agglomerating tendency and/or protein-membrane interactions. However, the possibility of self-cleaning action by proteolytic enzymes can't be ruled out, because both B-like and D-like enzymes are more active at the lower pH range examined. There was no significant difference in the rejection of D-like cathepsin due to the molecular weight of this enzyme being above the exclusion limit of the PM30 membrane used. The apparent rejectivity of B-like cathepsin appeared to decrease with decreasing pH, which was likely an artifact caused by enzyme inactivation at lower pH, because the levels of B-like cathepsin activity in all permeates were similar (not shown). B-like cathepsin is less stable than D-like cathepsin at low pH range. The most stable pH ranges of B-like and D-like cathepsins were determined in chapter 2 as 3–6 and 2.5–5, respectively.

TABLE 26

The effect of feed pH on solute rejection of acidified clam viscera extract

| pH | % Rejection | | | |
|---|---|---|---|---|
| | Solids | Proteins | Cathepsins D-like | Cathepsins B-like |
| 2.5 | 5.99 | 52.54 | 98.09 | 79.79 |
| 3.2 | 6.23 | 57.78 | 99.93 | 84.20 |
| 4.0 | 6.64 | 68.01 | 95.89 | 90.16 |
| 5.0 | 7.04 | 71.90 | 96.92 | 94.07 |

The effect of feed pH on the membrane flux is shown in FIG. 9. The lines seem unlikely to converge. The magnitude of x-intercept increases with decreasing pH, indicating that higher solute concentration is required to form the gel at lower pH, which is likely a consequence of increasing repulsive forces between more positively-charged macrosolutes. Notice that at pH 2.5 the curvature of the line continues through the entire concentration range, suggesting that a true gel layer has never been formed even at the end of the run. The decrease in pH appeared to reduce apparent mass transfer coefficient, likely because the permeability of a gel layer formed at higher concentration is lower than at lower concentration. The flux, on the other hand, increased with decreasing pH due to the larger driving force provided by high gel concentration on the membrane surface.

10. The effect of pressure

Solute retentivity appeared to be independent of operation pressure except at the lowest pressure examined (Table 27). Under low pressure condition, membrane or gel layer is less rigid and compact, resulting in an increase of solute flux through the gel layer and membrane. Better separation of D-like and B-like cathepsins was observed at the lowest pressure probably due to the fact that a less rigid gel layer or membrane allows more free passage of B-like cathepsin which has a molecular weight well below the exclusion limit of the membrane, while D-like cathepsin with a molecular weight above the exclusion limit is retained in any condition.

The apparent mass transfer coefficient increases with increasing pressure probably due to increased solute diffusivity which is a consequence of lower apparent gel concentration at higher pressure environment. The membrane flux increased with increasing pressure, but reduced flux occurred at 45 psig possibly due to membrane or gel layer over-compaction. One might suspect that the lower rejection at 15 psig is an artifact of enzyme inactivation due to longer exposure of enzymes in order to achieve same degree of concentration. However, this was not the case, since the enzyme activity of both enzymes proportionally increased in the ultrafiltrate.

11. The effect of recirculation rate

Shear damage to protein products such as enzymes has been reported during laboratory scale ultrafiltration (Charm and Lai, 1971, Biotech. & Bioengin., 13: 185; Korues and Olson, 1977, Biotech. & Bioengin., 19: 1). Its avoidance is often sought by setting low limits on the retentate recirculation rates and by specifying expensive pumps known to be associated with low shear action, because high velocity gradients in the vicinity of interfaces may be associated with structural damage due to adsorption and interfacial effects (Virkar et al., 1981, Biotech & Bioengin., 23: 425). On the other hand, it is desirable to operate at the highest possible recirculation rate, which minimizes concentration polarization and membrane fouling, allowing maximum membrane throughput.

Despite no significant difference for solids and protein retentivity, the retentivity of enzymes, especially B-like cathepsin, increased with increasing recirculation rate (Table 28). Better fractionation of D-like and B-like cathepsins appeared at lower recirculation rate, which was consistent with the observation that lower apparent gel concentration was associated with higher recirculation rate. Since the molecular weight above the exclusion limit of the membrane. Increased gel concentration on the membrane surface hinders the transport of B-like cathepsin to the membrane surface, thus reduces the fractionation ability of the membrane. Both enzymes appeared very stable under the highest shear condition examined.

The increase in apparent gel concentration with increased recirculation rate can be realized because the increasing shear rate associated with increasing fluid velocity reduces the fluid viscosity. The apparent mass transfer coefficients were similar for each recirculation rate. The observation suggests that the decrease in solute diffusivity as a result of increase in apparent gel concentration offset the decrease in boundary layer thickness as a result of increase in shear rate, thus no significant differences were observed from apparent mass transfer coefficient, which is the ratio of solute diffusivity to boundary layer thickness.

TABLE 28

The effect of recirculation rate on solute rejection of acidified clam viscera extract

| Recirculation rate (ml/min) | % Rejection | | | |
|---|---|---|---|---|
| | Solids | Proteins | Cathepsins D-like | B-like |
| 100 | 5.96 | 56.28 | 86.11 | 44.96 |
| 160 | 5.61 | 56.17 | 90.73 | 56.82 |
| 200 | 6.23 | 57.78 | 99.93 | 84.20 |
| 360* | 5.72 | 58.06 | 98.53 | 94.09 |

*Extensive foaming of retentate during the ultrafiltration run.

12. Conclusions

Both ultrafiltration flux and solute retentivity were affected by membrane type as well as operational parameters such as pH, temperature, pressure and recirculation rate. Acidified clam viscera extract could be concentrated quickly by selecting a more hydraulic permeable membrane and then operating the system at low pH range with sufficient pressure and high recirculation rate. At the expense of reduced flux rate, the separation of D-like and B-like cathepsins appeared feasible when operating the system at lower pressure and reduced recirculation rate.

It should be understood that the enzymes described about can be isolated and characterized by equivalent means other than those specifically above. Likewise the enzymes can be employed in ways within the skill of the art other than specifically exemplified.

We claim:

1. A composition comprising, in at least partially purified form, a carboxyl proteinase enzyme, extracted from surf clam or cherrystone clam viscera, having a molecular weight of about 77,200 determined chromatographically against standard proteins, which enzyme is stable from pH 2.5 to pH 5.0 and has the following activities: optimum activity toward casein at pH 2.2 and hemoglobin at pH 2.5–2.8; insensitive to heavy metals; strongly inhibited by pepstatin; insensitive to soybean trypsin inhibitor, phenylmethanesulphonylfluoride, and 4-chloromercuribenzoate; insensitive to diazoacetylnorleucine methyl ester in the presence of cupric ions; active against casein, bovine serum albumin and fibrinogen and substantially more active against hemoglobin as compared to casein, bovine serum albumin and fibrinogen inactive against the insoluble substrates, collagen, elastin, fibrin; and inactive against α-benzoyl-DL-arginine p-nitroanilide.

2. A composition comprising, in at least partially purified form, a carboxyl proteinase enzyme, extracted from surf clam or cherrystone clam viscera, having a molecular weight of about 36,700 determined chromatographically against standard proteins, which enzyme is stable from pH 2.5 to pH 5.0 and has the following activites: optimum activity toward casein at pH 2.2 and hemoglobin at pH 2.5–2.8; insensitive to heavy metals, strongly inhibited by pepstatin; insensitive to soybean trypsin inhibitor, phenylmethanesulphonylfluoride, and 4-chloromercuribenzoate; insensitive to diazoacetylnorleucine methyl ester in the presence of cupric ions; active agaist casein, bovine serum albumin and fibrinogen and substantially more active against hemoglobin as compared to casein, bovine serum albumin and fibrinogen; inactive against the insoluble substrates, collagen, elastin, fibrin; and inactive against α-benzoyl-DL-arginine p-nitroanilide.

3. A composition comprising, in at least partially purified form, a thiol proteinase enyzme, extracted from surf clam or cherrystone clam viscera, having a molecular weight of about 17,400 determined chromatographically against standard proteins, which enzyme is stable from pH 3.0 to pH 6.0 and has the following activities; optimum activity toward hemoglobin at pH 2.8 and toward casein at pH 2.8 and pH 5.5–5.8; sensitive to cupric ion and mercuric ion; slightly inhibited by Pb++; sensitive to diazoacetylnorleucine methyl ester in the presence of cupric ion; inhibited by phenylmethanesulphonylfluoride iodoacetomide, tosyl-phenylalanine chloromethyl ketone, tosyl-lysine chloromethyl ketone and leupeptin; not inhibited by trypsin inhibitors, active against casein, bovine serum albumin and fibrinogen and substantially more active against hemoglobin compared to casein, bovine serum albumin and fibrinogen inactive against the insoluble substrates, collagen, elastin, fibrin; and active against 2-benzoyl-DL-arginine p-nitroanilide at pH 6.0–6.5.

4. A composition according to claims 1, 2 or 3 wherein the enzyme is isolated by a method which comprises extracting surf clam or cherrystone clam viscera with water, acidifying the resultant aqueous extract, stabilizing the aqueous extract with stabilizing amounts of chelating and reducing agents adapted to stabilize the enzyme, concentrating the stabilized aqueous composition and separating the enzyme.

5. The method of claim 4 wherein the separation of the enzyme is accomplished by ethanol fractionation followed by chromatographic separation.

* * * * *

UNITED STATES PATENT AND TRADEMARK OFFICE
CERTIFICATE OF CORRECTION

PATENT NO.  : 4,677,069
DATED       : June 30, 1987
INVENTOR(S) : Chen et al.

It is certified that error appears in the above-identified patent and that said Letters Patent is hereby corrected as shown below:

Claim 1, Column 50, line 19, after "fibrinogen"
  insert --;--.

Claim 3, column 50, line 43, after "activities",
  insert --:-- and delete the semicolon.

Claim 3, column 50, line 47, "Pb++" should be --$Pb^{++}$--.

Signed and Sealed this

Thirteenth Day of October, 1987

Attest:

DONALD J. QUIGG

Attesting Officer

Commissioner of Patents and Trademarks